(12) United States Patent
Brevnova et al.

(10) Patent No.: US 11,352,610 B2
(45) Date of Patent: *Jun. 7, 2022

(54) DIACYLGLYCEROL ACYLTRANSFERASE (DGA1) POLYNUCLEOTIDES, AND METHODS OF INCREASING YEAST CELL LIPID PRODUCTION BY OVEREXPRESSION OF HETEROLOGOUS DGA1

(71) Applicant: Ginkgo Bioworks, Inc., Boston, MA (US)

(72) Inventors: Elena E. Brevnova, Belmont, MA (US); Arthur J. Shaw, IV, Belmont, MA (US); Emily H. Greenhagen, Melrose, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/288,544

(22) Filed: Feb. 28, 2019

(65) Prior Publication Data

US 2019/0316098 A1 Oct. 17, 2019

Related U.S. Application Data

(62) Division of application No. 15/120,952, filed as application No. PCT/US2015/017227 on Feb. 24, 2015, now Pat. No. 10,260,052.

(60) Provisional application No. 61/943,664, filed on Feb. 24, 2014.

(51) Int. Cl.
*C12N 9/10* (2006.01)
*C12P 7/6445* (2022.01)

(52) U.S. Cl.
CPC .......... *C12N 9/1029* (2013.01); *C12P 7/6445* (2013.01); *C12Y 203/0102* (2013.01)

(58) Field of Classification Search
CPC ... C12N 9/1029; C12N 9/10; C12Y 203/0102
See application file for complete search history.

(56) References Cited

U.S. PATENT DOCUMENTS

| | | | |
|---|---|---|---|
| 6,791,008 B1 | 9/2004 | Banas et al. | |
| 10,260,052 B2 * | 4/2019 | Brevnova | C12Y 203/0102 |
| 2006/0094086 A1 | 5/2006 | Yadav et al. | |
| 2011/0047659 A1 | 2/2011 | Daley et al. | |
| 2012/0058246 A1 | 3/2012 | Meyer et al. | |
| 2012/0301932 A1 | 11/2012 | Hong et al. | |

FOREIGN PATENT DOCUMENTS

| | | |
|---|---|---|
| CN | 101437953 | 5/2009 |
| EP | 2620500 | 7/2013 |
| WO | WO-2009/143401 A2 | 11/2009 |
| WO | WO 2011/061629 | 5/2011 |

OTHER PUBLICATIONS

Zhu et al., "A multi-omic map of the lipid-producing yeast Rhodosporidium toruloides," Nature Communications, 3: Article No. 1112 (2012).
Accession No. AB453835.1, "Cloning and functional characterization of diacylglycerol acyltransferase gene from Rhodosporidium Toruloides: European nucleotide archive (ENA)," Jul. 23, 2009.
International Preliminary Report on Patentability for International Application No. PCT/US2015/017557, dated Sep. 9, 2016.
Office Action issued in Corresponding Chinese Patent Application No. 201580021065, dated Apr. 15, 2019. (English Translation).

* cited by examiner

*Primary Examiner* — Tekchand Saidha
(74) *Attorney, Agent, or Firm* — Foley Hoag LLP; Janine Ladislaw; Mohanad Mossalam

(57) ABSTRACT

DGA1 catalyzes the final enzymatic step for converting acyl-CoA and 1,2-diacylglycerol to triacylglycerols (TAG) and CoA in yeast. Disclosed are methods for expression in an oleaginous yeast host of polynucleotide sequences encoding DGA1 from *Rhodosporidium toruloides, Lipomyces starkeyi, Aurantiochytrium limacinum, Aspergillus terreus*, or *Claviceps purpurea*. Also described herein are engineered recombinant host cells of *Yarrowia lipolytica* comprising heterologous DGA1 polynucleotides encoding DGA1 proteins, or functionally active portions thereof, having the capability of producing increased lipid production and possessing the characteristic of enhanced glucose consumption efficiency.

15 Claims, 2 Drawing Sheets

Specification includes a Sequence Listing.

SEQUENCE LISTING

```
<160> NUMBER OF SEQ ID NOS: 18

<210> SEQ ID NO 1
<211> LENGTH: 514
<212> TYPE: PRT
<213> ORGANISM: Yarrowia lipolytica

<400> SEQUENCE: 1

Met Thr Ile Asp Ser Gln Tyr Tyr Lys Ser Arg Asp Lys Asn Asp Thr
1               5                   10                  15

Ala Pro Lys Ile Ala Gly Ile Arg Tyr Ala Pro Leu Ser Thr Pro Leu
            20                  25                  30

Leu Asn Arg Cys Glu Thr Phe Ser Leu Val Trp His Ile Phe Ser Ile
        35                  40                  45

Pro Thr Phe Leu Thr Ile Phe Met Leu Cys Cys Ala Ile Pro Leu Leu
    50                  55                  60

Trp Pro Phe Val Ile Ala Tyr Val Val Tyr Ala Val Lys Asp Asp Ser
65                  70                  75                  80

Pro Ser Asn Gly Gly Val Val Lys Arg Tyr Ser Pro Ile Ser Arg Asn
```

```
                        85                  90                  95
Phe Phe Ile Trp Lys Leu Phe Gly Arg Tyr Phe Pro Ile Thr Leu His
                100                 105                 110
Lys Thr Val Asp Leu Glu Pro Thr His Thr Tyr Tyr Pro Leu Asp Val
            115                 120                 125
Gln Glu Tyr His Leu Ile Ala Glu Arg Tyr Trp Pro Gln Asn Lys Tyr
        130                 135                 140
Leu Arg Ala Ile Ile Thr Thr Ile Glu Tyr Phe Leu Pro Ala Phe Met
145                 150                 155                 160
Lys Arg Ser Leu Ser Ile Asn Glu Gln Glu Gln Pro Ala Glu Arg Asp
                165                 170                 175
Pro Leu Leu Ser Pro Val Ser Pro Ser Pro Gly Ser Gln Pro Asp
                180                 185                 190
Lys Trp Ile Asn His Asp Ser Arg Tyr Ser Arg Gly Glu Ser Ser Gly
                195                 200                 205
Ser Asn Gly His Ala Ser Gly Ser Glu Leu Asn Gly Asn Gly Asn Asn
        210                 215                 220
Gly Thr Thr Asn Arg Arg Pro Leu Ser Ser Ala Ser Ala Gly Ser Thr
225                 230                 235                 240
Ala Ser Asp Ser Thr Leu Leu Asn Gly Ser Leu Asn Ser Tyr Ala Asn
                245                 250                 255
Gln Ile Ile Gly Glu Asn Asp Pro Gln Leu Ser Pro Thr Lys Leu Lys
                260                 265                 270
Pro Thr Gly Arg Lys Tyr Ile Phe Gly Tyr His Pro His Gly Ile Ile
                275                 280                 285
Gly Met Gly Ala Phe Gly Gly Ile Ala Thr Glu Gly Ala Gly Trp Ser
        290                 295                 300
Lys Leu Phe Pro Gly Ile Pro Val Ser Leu Met Thr Leu Thr Asn Asn
305                 310                 315                 320
Phe Arg Val Pro Leu Tyr Arg Glu Tyr Leu Met Ser Leu Gly Val Ala
                325                 330                 335
Ser Val Ser Lys Lys Ser Cys Lys Ala Leu Leu Lys Arg Asn Gln Ser
                340                 345                 350
Ile Cys Ile Val Val Gly Gly Ala Gln Glu Ser Leu Leu Ala Arg Pro
        355                 360                 365
Gly Val Met Asp Leu Val Leu Leu Lys Arg Lys Gly Phe Val Arg Leu
        370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Ser Lys Leu
                405                 410                 415
Tyr Arg Phe Gln Gln Phe Val Lys Asn Phe Leu Gly Phe Thr Leu Pro
                420                 425                 430
Leu Met His Ala Arg Gly Val Phe Asn Tyr Asp Val Gly Leu Val Pro
                435                 440                 445
Tyr Arg Arg Pro Val Asn Ile Val Val Gly Ser Pro Ile Asp Leu Pro
        450                 455                 460
Tyr Leu Pro His Pro Thr Asp Glu Glu Val Ser Glu Tyr His Asp Arg
465                 470                 475                 480
Tyr Ile Ala Glu Leu Gln Arg Ile Tyr Asn Glu His Lys Asp Glu Tyr
                485                 490                 495
Phe Ile Asp Trp Thr Glu Glu Gly Lys Gly Ala Pro Glu Phe Arg Met
                500                 505                 510
```

Ile Glu

<210> SEQ ID NO 2
<211> LENGTH: 1545
<212> TYPE: DNA
<213> ORGANISM: Yarrowia lipolytica

<400> SEQUENCE: 2

```
atgactatcg actcacaata ctacaagtcg cgagacaaaa acgacacggc acccaaaatc    60
gcgggaatcc gatatgcccc gctatcgaca ccattactca accgatgtga gaccttctct   120
ctggtctggc acattttcag cattcccact ttcctcacaa ttttcatgct atgctgcgca   180
attccactgc tctggccatt tgtgattgcg tatgtagtgt acgctgttaa agacgactcc   240
ccgtccaacg gaggagtggt caagcgatac tcgcctattt caagaaactt cttcatctgg   300
aagctctttg gccgctactt ccccataact ctgcacaaga cggtggatct ggagcccacg   360
cacacatact accctctgga cgtccaggag tatcacctga ttgctgagag atactggccg   420
cagaacaagt acctccgagc aatcatcacc accatcgagt actttctgcc cgccttcatg   480
aaacggtctc tttctatcaa cgagcaggag cagcctgccg agcgagatcc tctcctgtct   540
cccgtttctc ccagctctcc gggttctcaa cctgacaagt ggattaacca cgacagcaga   600
tatagccgtg gagaatcatc tggctccaac ggccacgcct cgggctccga acttaacggc   660
aacggcaaca atggcaccac taaccgacga cctttgtcgt ccgcctctgc tggctccact   720
gcatctgatt ccacgcttct taacgggtcc ctcaactcct acgccaacca gatcattggc   780
gaaaacgacc cacagctgtc gcccacaaaa ctcaagccca ctggcagaaa atacatcttc   840
ggctaccacc cccacggcat tatcggcatg ggagcctttg gtggaattgc accgagggga   900
gctggatggt ccaagctctt tccgggcatc cctgtttctc ttatgactct caccaacaac   960
ttccgagtgc ctctctacag agagtacctc atgagtctgg gagtcgcttc tgtctccaag  1020
aagtcctgca aggccctcct caagcgaaac cagtctatct gcattgtcgt tggtggagca  1080
caggaaagtc ttctggccag acccggtgtc atggacctgg tgctactcaa gcgaaagggt  1140
tttgttcgac ttggtatgga ggtcggaaat gtcgcccttg ttcccatcat ggcctttggt  1200
gagaacgacc tctatgacca ggttagcaac gacaagtcgt ccaagctgta ccgattccag  1260
cagtttgtca gaacttcct tggattcacc cttcctttga tgcatgcccg aggcgtcttc  1320
aactacgatg tcggtcttgt cccctacagg cgacccgtca acattgtggt tggttccccc  1380
attgacttgc cttatctccc acaccccacc gacgaagaag tgtccgaata ccacgaccga  1440
tacatcgccg agctgcagcg aatctacaac gagcacaagg atgaatattt catcgattgg  1500
accgaggagg gcaaaggagc cccagagttc cgaatgattg agtaa          1545
```

<210> SEQ ID NO 3
<211> LENGTH: 348
<212> TYPE: PRT
<213> ORGANISM: Rhodosporidium toruloides

<400> SEQUENCE: 3

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45
```

```
Gly Val Phe Leu Leu Cys Ser Phe Pro Pro Leu Trp Pro Ala Val
     50                  55                  60
Ile Ala Tyr Leu Thr Trp Val Phe Phe Ile Asp Gln Ala Pro Ile His
 65                  70                  75                  80
Gly Gly Arg Ala Gln Ser Trp Leu Arg Lys Ser Arg Ile Trp Val Trp
                 85                  90                  95
Phe Ala Gly Tyr Tyr Pro Val Ser Leu Ile Lys Ser Ala Asp Leu Pro
            100                 105                 110
Pro Asp Arg Lys Tyr Val Phe Gly Tyr His Pro His Gly Val Ile Gly
        115                 120                 125
Met Gly Ala Ile Ala Asn Phe Ala Thr Asp Ala Thr Gly Phe Ser Thr
130                 135                 140
Leu Phe Pro Gly Leu Asn Pro His Leu Leu Thr Leu Gln Ser Asn Phe
145                 150                 155                 160
Lys Leu Pro Leu Tyr Arg Glu Leu Leu Ala Leu Gly Ile Cys Ser
                165                 170                 175
Val Ser Met Lys Ser Cys Gln Asn Ile Leu Arg Gln Gly Pro Gly Ser
            180                 185                 190
Ala Leu Thr Ile Val Val Gly Gly Ala Ala Glu Ser Leu Ser Ala His
        195                 200                 205
Pro Gly Thr Ala Asp Leu Thr Leu Lys Arg Arg Lys Gly Phe Ile Lys
210                 215                 220
Leu Ala Ile Arg Gln Gly Ala Asp Leu Val Pro Val Phe Ser Phe Gly
225                 230                 235                 240
Glu Asn Asp Ile Phe Gly Gln Leu Arg Asn Glu Arg Gly Thr Arg Leu
                245                 250                 255
Tyr Lys Leu Gln Lys Arg Phe Gln Gly Val Phe Gly Phe Thr Leu Pro
            260                 265                 270
Leu Phe Tyr Gly Arg Gly Leu Phe Asn Tyr Asn Val Gly Leu Met Pro
        275                 280                 285
Tyr Arg His Pro Ile Val Ser Val Val Gly Arg Pro Ile Ser Val Glu
290                 295                 300
Gln Lys Asp His Pro Thr Thr Ala Asp Leu Glu Glu Val Gln Ala Arg
305                 310                 315                 320
Tyr Ile Ala Glu Leu Lys Arg Ile Trp Glu Glu Tyr Lys Asp Ala Tyr
                325                 330                 335
Ala Lys Ser Arg Thr Arg Glu Leu Asn Ile Ile Ala
            340                 345

<210> SEQ ID NO 4
<211> LENGTH: 1858
<212> TYPE: DNA
<213> ORGANISM: Rhodosporidium toruloides

<400> SEQUENCE: 4
atgggccagc aggcgacgcc cgaggagcta tacacacgct cagagatctc caagatcaag      60
caagtcgagc cagctcttct cctcaccacc ccacaacata ccccgcagcc cacgacagcc     120
ctcccacagc acctgcagcc tgctgaccag ctcgagaaca cccacagatt cgcacccttt     180
ggcgtcccgc ggtcgcgccg gctgcagacc ttctccgtct ttgcctggac gacggcactg     240
cccatcctac tcggcgtctt cttcctcctc tggtgcgtca ggcttggcgt gatctgagag     300
tagcgggcgg atcatctgac ctgcttcttc gctgcagctc gttccaccg ctctggccgg     360 ctgtcattgc ctacctcacc tgggtctttt tcattgacca ggcgccgatt cacggtggac     420
```

```
gggcgcagtc ttggctgcgg aagagtcgga tatgggtctg gtttgcagga tactatcccg      480
tcaggtgcgt cctctttcca agcctgcgtc tcgaggcctc gctcacggcc aactcgcccg      540
accggctacc tccgaacttt ccgtcaacag cttgatcaag gtcagtctgc gcgtctctcg      600
acttcagtgc tctgtggagg agctgcgcca ttgggcccga cctgcggagg gcctcaaagg      660
acgatgccgc tgacttcctt tcctccgaca gagcgccgac ttgccgcctg accggaagta      720
cgtctttggc taccacccgc acggcgtcat aggcatgggc gccatcgcca acttcgcgac      780
cgacgcaacc ggcttctcga cactcttccc cggcttgaac cctcacctcc tcaccctcca      840
aagcaacttc aagctcccgc tctaccgcga gttgctgctc gctctcggca tatgctccgt      900
ctcgatgaag agctgtcaga acattctgcg acaaggtgag cggtatgcgc aagacgggcg      960
gtcaagcgtg aacgcagtga cgagaagag ctgaccttcc gccttactcc atccgtgcag     1020
gtcctggctc ggctctcact atcgtcgtcg gtggcgccgc cgagagcttg agtgcgcatc     1080
ccggaaccgc cgatcttacg ctcaagcgac gaaaaggctt catcaaactc gcgatccggc     1140
aaggcgccga ccttgtgccc gtcttttcgt tcggcgagaa cgacgtgcgc acgctctccg     1200
agtctctaaa ccggaagcga atgctgaccg ctgcccaatt ctctctccag atctttggcc     1260
agctgcgaaa cgagcgagga acgcggctgt acaagttgca gaagcgtttc caaggcgtgt     1320
ttggcttcac cctccgtacg tctcaccgcg ccgtcttgcc gaactgctcg ttcagtcgct     1380
cacgcagctt tcactcgcgc agctctcttc tacggccggg gactcttcaa ctgtgcgctc     1440
gagttcaccg cttcgccaac agcgaggaat gcctccgagt acagcccagc tgacgccca     1500 tctcttctca tagacaacgt cggattgatg ccgtatcgcc atccgatcgt ctctgtcggt     1560
gtgaacccgc tctgtcgctc ctacctgcgt tccttaggct gacaccactc gcgtcaaaca     1620
gtcggtcgac caatctcggt agagcagaag gaccacccga ccacggcgga cctcgaagaa     1680
gttcaggcgc ggtatatcgc agaactcaag cggtacgttc aagtcgtct gcctccgctt     1740 gccgcctcaa ataagctgag gcgtgctgac cgtatctgcc gaaccgtaca gcatctggga     1800
agaatacaag gacgcctacg ccaaaagtcg cacgcgggag ctcaatatta tcgcctga     1858
```

<210> SEQ ID NO 5
<211> LENGTH: 348
<212> TYPE: PRT
<213> ORGANISM: Rhodosporidium toruloides

<400> SEQUENCE: 5

```
Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
```

```
              115                 120                 125
Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335

Ala Lys Ser Arg Thr Arg Glu Leu Asn Ile Ile Ala
            340                 345

<210> SEQ ID NO 6
<211> LENGTH: 1047
<212> TYPE: DNA
<213> ORGANISM: Rhodosporidium toruloides

<400> SEQUENCE: 6
atgggccagc aggcgacgcc cgaggagcta tacacacgct cagagatctc caagatcaag      60
ttcgcaccct ttggcgtccc gcggtcgcgc cggctgcaga ccttctccgt ctttgcctgg     120
acgacggcac tgcccatcct actcggcgtc ttcttcctcc tctgctcgtt cccaccgctc     180
tggccggctg tcattgccta cctcacctgg gtcttttttca ttgaccaggc gccgattcac     240
ggtggacggg cgcagtcttg gctgcggaag agtcggatat gggtctggtt tgcaggatac     300
tatcccgtca gcttgatcaa gagcgccgac ttgccgcctg accggaagta cgtctttggc     360 taccaccgc acggcgtcat aggcatgggc gccatcgcca acttcgcgac cgacgcaacc     420
ggcttctcga cactcttccc cggcttgaac cctcacctcc tcaccctcca aagcaacttc     480
aagctcccgc tctaccgcga gttgctgctc gctctcggca tgctccgt ctcgatgaag       540 agctgtcaga acattctgcg acaaggtcct ggctcggctc tcactatcgt cgtcggtggc      600
gccgccgaga gcttgagtgc gcatcccgga accgccgatc ttacgctcaa gcgacgaaaa     660
ggcttcatca aactcgcgat ccggcaaggc gccgaccttg tcccgtcttt tcgttcggc      720 gagaacgaca tctttggcca gctgcgaaac gagcgaggaa cgcggctgta caagttgcag     780
aagcgtttcc aaggcgtgtt tggcttcacc ctccctctct tctacggccg ggactcttc      840
```

```
aactacaacg tcggattgat gccgtatcgc catccgatcg tctctgtcgt cggtcgacca    900
atctcggtag agcagaagga ccacccgacc acggcggacc tcgaagaagt tcaggcgcgg    960
tatatcgcag aactcaagcg gatctgggaa gaatacaagg acgcctacgc caaaagtcgc   1020
acgcgggagc tcaatattat cgcctga                                       1047

<210> SEQ ID NO 7
<211> LENGTH: 348
<212> TYPE: PRT
<213> ORGANISM: Rhodosporidium toruloides

<400> SEQUENCE: 7

Met Gly Gln Gln Ala Thr Pro Glu Glu Leu Tyr Thr Arg Ser Glu Ile
1               5                   10                  15

Ser Lys Ile Lys Phe Ala Pro Phe Gly Val Pro Arg Ser Arg Arg Leu
            20                  25                  30

Gln Thr Phe Ser Val Phe Ala Trp Thr Thr Ala Leu Pro Ile Leu Leu
        35                  40                  45

Gly Val Phe Phe Leu Leu Cys Ser Phe Pro Pro Leu Trp Pro Ala Val
    50                  55                  60

Ile Ala Tyr Leu Thr Trp Val Phe Phe Ile Asp Gln Ala Pro Ile His
65                  70                  75                  80

Gly Gly Arg Ala Gln Ser Trp Leu Arg Lys Ser Arg Ile Trp Val Trp
                85                  90                  95

Phe Ala Gly Tyr Tyr Pro Val Ser Leu Ile Lys Ser Ala Asp Leu Pro
            100                 105                 110

Pro Asp Arg Lys Tyr Val Phe Gly Tyr His Pro His Gly Val Ile Gly
        115                 120                 125

Met Gly Ala Ile Ala Asn Phe Ala Thr Asp Ala Thr Gly Phe Ser Thr
    130                 135                 140

Leu Phe Pro Gly Leu Asn Pro His Leu Leu Thr Leu Gln Ser Asn Phe
145                 150                 155                 160

Lys Leu Pro Leu Tyr Arg Glu Leu Leu Leu Ala Leu Gly Ile Cys Ser
                165                 170                 175

Val Ser Met Lys Ser Cys Gln Asn Ile Leu Arg Gln Gly Pro Gly Ser
            180                 185                 190

Ala Leu Thr Ile Val Val Gly Gly Ala Ala Glu Ser Leu Ser Ala His
        195                 200                 205

Pro Gly Thr Ala Asp Leu Thr Leu Lys Arg Arg Lys Gly Phe Ile Lys
    210                 215                 220

Leu Ala Ile Arg Gln Gly Ala Asp Leu Val Pro Val Phe Ser Phe Gly
225                 230                 235                 240

Glu Asn Asp Ile Phe Gly Gln Leu Arg Asn Glu Arg Gly Thr Arg Leu
                245                 250                 255

Tyr Lys Leu Gln Lys Arg Phe Gln Gly Val Phe Gly Phe Thr Leu Pro
            260                 265                 270

Leu Phe Tyr Gly Arg Gly Leu Phe Asn Tyr Asn Val Gly Leu Met Pro
        275                 280                 285

Tyr Arg His Pro Ile Val Ser Val Val Gly Arg Pro Ile Ser Val Glu
    290                 295                 300

Gln Lys Asp His Pro Thr Thr Ala Asp Leu Glu Glu Val Gln Ala Arg
305                 310                 315                 320

Tyr Ile Ala Glu Leu Lys Arg Ile Trp Glu Glu Tyr Lys Asp Ala Tyr
                325                 330                 335
```

Ala Lys Ser Arg Thr Arg Glu Leu Asn Ile Ile Ala
            340                 345

<210> SEQ ID NO 8
<211> LENGTH: 1047
<212> TYPE: DNA
<213> ORGANISM: Rhodosporidium toruloides

<400> SEQUENCE: 8
atgggacagc aggctacccc cgaggagctc tacacccgat ccgagatttc taagattaag      60 ttcgccccctt ttggagtgcc ccgatcccga cgactccaga ccttctccgt ttttgcctgg    120
accactgctc tgcccattct gctcggcgtc ttctttctgc tctgctcttt cccccctctc    180
tggcccgccg tcatcgctta cctgacctgg gtgttcttta cgaccaggc ccctattcac    240 ggcggtcgag ctcagtcctg gctgcgaaag tctcgaattt gggtttggtt cgccggttac    300
taccccgtct ctctcatcaa gtcggctgac ctgcccctg atcgaaagta cgtgttcggc    360
taccaccctc atggtgttat cggtatggga gccattgcta actttgccac cgatgctact    420
ggtttctcca ccctctttcc cggactgaac cctcacctgc tcactctcca gtctaacttc    480
aagctccccc tgtaccgaga gctgctcctg gccctggta tctgctccgt ctctatgaag    540
tcttgtcaga acattctccg cagggacct ggttcggctc tgaccatcgt cgtgggagga    600
gctgctgagt cgctctccgc ccatcctgga accgctgacc tcactctgaa gacgaaaag   660 ggcttcatca agctcgccat cgacagggt gctgacctgg tgcccgtttt ctcctttgga   720
gagaacgata ttttcggcca gctgcgaaac gagcgaggaa cccgactcta caagctgcag   780
aagcgatttc agggtgtgtt cggcttcacc ctccctctgt tctacggacg aggcctcttt   840
aactacaacg ttggactgat gcctaccga caccctatcg tctcggttgt cggccgaccc   900
atttccgtgg agcagaagga ccatcctacc actgccgatc tcgaggaggt gcaggcccga   960
tacatcgctg agctgaagcg aatttgggag gagtacaagg acgcctacgc taagtctcga  1020
acccgagagc tgaacatcat tgcctaa                                       1047

<210> SEQ ID NO 9
<211> LENGTH: 410
<212> TYPE: PRT
<213> ORGANISM: Lipomyces starkeyi

<400> SEQUENCE: 9

Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser
65                  70                  75                  80

Asn Gly Glu Ile Ser Arg Arg Arg Ser Pro Leu Phe Arg Arg Leu Pro
            85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
            115                 120                 125

```
Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240

Asp Gln Ser Ile Cys Ile Val Ile Gly Gly Ala Gln Glu Ser Leu Leu
                245                 250                 255

Ala Glu Pro Gly Thr Leu Asp Leu Ile Leu Val Lys Arg Arg Gly Phe
            260                 265                 270

Val Lys Leu Ala Met Ser Thr Ala Arg Val Ser Asp Gln Pro Ile Cys
        275                 280                 285

Leu Val Pro Ile Leu Ser Phe Gly Glu Asn Asp Val Tyr Asp Gln Val
    290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Tyr Phe Val Asp His Lys Ser Gly Lys Gly
385                 390                 395                 400

Val Lys Asn Ser Glu Met Arg Phe Val Glu
                405                 410

<210> SEQ ID NO 10
<211> LENGTH: 1233
<212> TYPE: DNA
<213> ORGANISM: Lipomyces starkeyi

<400> SEQUENCE: 10
atgagtgaga aggcagagat cgaggttccg ccgcaaaaat cgacattccc tcgcagtgtg      60
cacttcgctc cacttcatat tccactggag agacgcctac agactttggc agtcttattc     120
cacactgtcg cgctaccata ctgcatcggt ctgttctttc tcatgctcgc gttccctcct     180
ttttggccat tattggtaat gtatgtcata tacgcatacg ggttcgacca ctcgagctcg     240
aacgagagat ctcccgccg gcgatcgccg ctgtttcgaa gactcccgtt gttcaggctg      300
tattgtgatt acttccccat ccacattcac cgggaggttc cgctcgagcc gacgtttcct     360
ggtcgccttc gcgaaccgag tggccttgtc gagcggtgga ttgcgaagat gttcggcgtg     420
caggacgctg ttgtcgaggg aaatgaatct gacgttaagg ccacggccaa cggcaatggg     480
```

```
acgacgaaag aaatcggacc gacgtatgtt tcggctatc atccgcatgg aattgttagc    540
ttgggtgcgt ttggtgctat tggtacggaa ggcgctggat gggagaagct ctttcctggg    600
atcccggtgt cactgctgac tctcgaaaca aatttcagcc ttccatttta cagagagtat    660
ttgctgtcac ttgggattgc ttcagtatct cgacggtctt gtaccaatct cctcaaacac    720
gaccaatcca tctgcatcgt tatcggcggc gcccaagagt cgctcttagc ggaaccaggc    780
actctagatc tgatcctcgt taaacgtcgc ggttttgtca aacttgcaat gtcaacggcg    840
cgggtatctg accaaccgat ttgtcttgtt ccgatcctca gtttcggcga aacgacgtg     900
tacgaccaag tccgcgggga ccgatcgtcg aagttgtata agatccagac ttttatcaag    960
aaagcggccg ggtttacgct accattgatg tatgcgcgcg gtatatttaa ttacgacttt   1020
gggctgatgc cgtaccgcag gcaaatgacg ctcgtggtcg gcaagccgat tgcagtgccg   1080
tacgtggccc agcctacgga ggctgaaatc gaagtgtatc acaagcagta catggatgaa   1140
ttgaggaggt tatgggacac gtataaggac gactattttg tagaccacaa gggcaagggg   1200
gtcaagaatt ccgagatgcg tttgtggag taa                                 1233
```

<210> SEQ ID NO 11
<211> LENGTH: 410
<212> TYPE: PRT
<213> ORGANISM: Lipomyces starkeyi

<400> SEQUENCE: 11

```
Met Ser Glu Lys Ala Glu Ile Glu Val Pro Pro Gln Lys Ser Thr Phe
1               5                   10                  15

Pro Arg Ser Val His Phe Ala Pro Leu His Ile Pro Leu Glu Arg Arg
            20                  25                  30

Leu Gln Thr Leu Ala Val Leu Phe His Thr Val Ala Leu Pro Tyr Cys
        35                  40                  45

Ile Gly Leu Phe Phe Leu Met Leu Ala Phe Pro Pro Phe Trp Pro Leu
    50                  55                  60

Leu Val Met Tyr Val Ile Tyr Ala Tyr Gly Phe Asp His Ser Ser
65                  70                  75                  80

Asn Gly Glu Ile Ser Arg Arg Arg Ser Pro Leu Phe Arg Arg Leu Pro
                85                  90                  95

Leu Phe Arg Leu Tyr Cys Asp Tyr Phe Pro Ile His Ile His Arg Glu
            100                 105                 110

Val Pro Leu Glu Pro Thr Phe Pro Gly Arg Leu Arg Glu Pro Ser Gly
        115                 120                 125

Leu Val Glu Arg Trp Ile Ala Lys Met Phe Gly Val Gln Asp Ala Val
    130                 135                 140

Val Glu Gly Asn Glu Ser Asp Val Lys Ala Thr Ala Asn Gly Asn Gly
145                 150                 155                 160

Thr Thr Lys Glu Ile Gly Pro Thr Tyr Val Phe Gly Tyr His Pro His
                165                 170                 175

Gly Ile Val Ser Leu Gly Ala Phe Gly Ala Ile Gly Thr Glu Gly Ala
            180                 185                 190

Gly Trp Glu Lys Leu Phe Pro Gly Ile Pro Val Ser Leu Leu Thr Leu
        195                 200                 205

Glu Thr Asn Phe Ser Leu Pro Phe Tyr Arg Glu Tyr Leu Leu Ser Leu
    210                 215                 220

Gly Ile Ala Ser Val Ser Arg Arg Ser Cys Thr Asn Leu Leu Lys His
225                 230                 235                 240
```

```
Asp Gln Ser Ile Cys Ile Val Ile Gly Gly Ala Gln Glu Ser Leu Leu
            245                 250                 255

Ala Glu Pro Gly Thr Leu Asp Leu Ile Leu Val Lys Arg Arg Gly Phe
        260                 265                 270

Val Lys Leu Ala Met Ser Thr Ala Arg Val Ser Asp Gln Pro Ile Cys
    275                 280                 285

Leu Val Pro Ile Leu Ser Phe Gly Glu Asn Asp Val Tyr Asp Gln Val
290                 295                 300

Arg Gly Asp Arg Ser Ser Lys Leu Tyr Lys Ile Gln Thr Phe Ile Lys
305                 310                 315                 320

Lys Ala Ala Gly Phe Thr Leu Pro Leu Met Tyr Ala Arg Gly Ile Phe
                325                 330                 335

Asn Tyr Asp Phe Gly Leu Met Pro Tyr Arg Arg Gln Met Thr Leu Val
            340                 345                 350

Val Gly Lys Pro Ile Ala Val Pro Tyr Val Ala Gln Pro Thr Glu Ala
        355                 360                 365

Glu Ile Glu Val Tyr His Lys Gln Tyr Met Asp Glu Leu Arg Arg Leu
    370                 375                 380

Trp Asp Thr Tyr Lys Asp Asp Tyr Phe Val Asp His Lys Gly Lys Gly
385                 390                 395                 400

Val Lys Asn Ser Glu Met Arg Phe Val Glu
                405                 410

<210> SEQ ID NO 12
<211> LENGTH: 1233
<212> TYPE: DNA
<213> ORGANISM: Lipomyces starkeyi

<400> SEQUENCE: 12
atgtccgaga aggctgagat tgaggtgccc ccccagaagt ctactttccc tcgatccgtt      60
catttcgccc cctgcatat cccctggag cgacgactcc agaccctggc tgtgctcttc      120
cacactgttg ccctgcctta ctgcatcgga ctcttctttc tgatgctcgc tttccccct      180 ttttggcccc tgctcgtgat gtacgttatc tacgcctacg gattcgacca ttcctcttcg      240
aacggcgaga tctctcgacg acgatcgcct ctgttccgac gactgcccct ctttcgactc      300
tactgtgatt acttccctat ccacattcat cgagaggtcc ccctggagcc tacctttcct      360
ggtcgactgc gagagcccttc cggactcgtt gagcgatgga ttgctaagat gttcggtgtc      420
caggacgccg tcgtggaggg aaacgagtct gatgtgaagg ccaccgctaa cggaaacggc      480
accactaagg agatcggccc tacttacgtc ttcggatacc accccatgg cattgtgtcc      540 ctgggagcct tggcgctat cggtaccgag ggtgctggat gggagaagct cttccctggt      600
attcccgtct cgctgctcac cctggagact aacttctccc tccccttta ccgagagtac      660 ctgctctctc tgggaatcgc ctcggtgtcc cgacgatcgt gcaccaacct gctcaagcac      720
gaccagtcta tctgtattgt tatcggaggt gctcaggagt ccctgctcgc tgagcctgga      780
accctggacc tcattctggt caagcgacga ggcttcgtga agctggccat gtccactgct      840
cgagtgtctg atcagcctat ttgcctggtt cccatcctct ctttcggcga aaacgacgtt      900
tacgatcagg tccgaggtga ccgatcctct aagctgtaca agattcagac cttcatcaag      960
aaggccgctg gctttactct ccctctgatg tacgcccgag gcatcttcaa ctacgacttt     1020
ggtctgatgc cctaccgacg acagatgacc ctcgttgtcg gcaagcctat tgccgtcccc     1080
tacgtggctc agcccactga ggccgagatc gaggtctacc acaagcagta catggacgag     1140
```

```
ctgcgacgac tctgggatac ctacaaggac gattacttcg ttgaccataa gggcaaggt      1200 gtcaagaact ctgagatgcg atttgtggag taa                                  1233
```

<210> SEQ ID NO 13
<211> LENGTH: 380
<212> TYPE: PRT
<213> ORGANISM: Aspergillus terreus

<400> SEQUENCE: 13

```
Met Pro Arg Asn Thr His Pro Pro Ala Asn Asn Ala Gly Pro Asn Ala
1               5                   10                  15

Ser His Lys Lys Asp Arg Lys Arg Gln Gly Arg Leu Phe Gln His Thr
            20                  25                  30

Val Pro Asn Lys Tyr Ser Arg Ile Arg Trp Ala Pro Leu Asn Ile Gly
        35                  40                  45

Leu Glu Arg Arg Leu Gln Thr Leu Val Val Leu Cys His Thr Leu Thr
    50                  55                  60

Ile Ala Leu Phe Leu Ala Phe Phe Phe Thr Cys Ala Ile Pro Leu
65                  70                  75                  80

Thr Trp Pro Leu Leu Phe Pro Tyr Leu Val Tyr Ile Thr Leu Phe Ser
                85                  90                  95

Thr Ala Pro Thr Ser Gly Thr Leu Lys Gly Arg Ser Asp Phe Leu Arg
            100                 105                 110

Ser Leu Pro Ile Trp Lys Leu Tyr Thr Ala Tyr Phe Pro Ala Lys Leu
        115                 120                 125

His Arg Ser Glu Pro Leu Leu Pro Thr Arg Lys Tyr Ile Phe Gly Tyr
    130                 135                 140

His Pro His Gly Ile Ile Ser His Gly Ala Phe Ala Ala Phe Ala Thr
145                 150                 155                 160

Asp Ala Leu Gly Phe Ser Lys Leu Phe Pro Gly Ile Thr Asn Thr Leu
                165                 170                 175

Leu Thr Leu Asp Ser Asn Phe Arg Ile Pro Phe Tyr Arg Glu Tyr Ala
            180                 185                 190

Met Ala Met Gly Val Ala Ser Val Ser Arg Glu Ser Cys Glu Asn Leu
        195                 200                 205

Leu Thr Lys Gly Gly Ala Asp Gly Glu Gly Met Gly Arg Ala Ile Thr
    210                 215                 220

Ile Val Val Gly Gly Ala Arg Glu Ser Leu Asp Ala Leu Pro His Thr
225                 230                 235                 240

Met Arg Leu Val Leu Lys Arg Lys Gly Phe Ile Lys Leu Ala Ile
                245                 250                 255

Arg Thr Gly Ala Asp Leu Val Pro Val Leu Ala Phe Gly Glu Asn Asp
            260                 265                 270

Leu Tyr Glu Gln Val Arg Ser Asp Gln His Pro Leu Ile Tyr Lys Val
    275                 280                 285

Gln Met Leu Val Lys Arg Phe Leu Gly Phe Thr Val Pro Leu Phe His
290                 295                 300

Ala Arg Gly Ile Phe Asn Tyr Asp Val Gly Leu Met Pro Tyr Arg Arg
305                 310                 315                 320

Pro Leu Asn Ile Val Val Gly Arg Pro Ile Gln Val Val Arg Gln Gln
                325                 330                 335

Asp Arg Asp Lys Ile Asp Asp Glu Tyr Ile Asp Arg Leu His Ala Glu
            340                 345                 350

Tyr Val Arg Glu Leu Glu Ser Leu Trp Asp Gln Trp Lys Asp Val Tyr
```

```
        355                 360                 365

Ala Lys Asp Arg Ile Ser Glu Leu Glu Ile Val Ala
    370                 375                 380

<210> SEQ ID NO 14
<211> LENGTH: 1143
<212> TYPE: DNA
<213> ORGANISM: Aspergillus terreus

<400> SEQUENCE: 14
atgccccgaa acacccaccc ccccgccaac aacgccggac ctaacgcctc tcacaagaag      60
gaccgaaagc gacagggacg actctttcag cacaccgttc ctaacaagta ctctcgaatc     120
cgatgggccc ccctcaacat tggcctggag cgacgactgc agaccctcgt cgtgctgtgc     180
cataccctca ctatcgccct gttcctcgct ttctttttct ttacttgtgc cattcccctg     240
acctggcctc tgctcttccc ctacctcgtg tacatcaccc tgttttcgac cgctcctact     300
tccggtaccc tgaagggacg atctgacttc ctccgatcgc tgcctatttg gaagctctac     360
actgcctact ttcccgctaa gctgcaccga tccgagcctc tgctccctac ccgaaagtac     420
atcttcggct accaccccca tggtatcatt tcccatggag ccttcgccgc ttttgccact     480
gacgctctcg gcttctctaa gctgtttcct ggtatcacca acactctgct caccctggat     540
tcgaacttcc gaattccctt ttaccgagag tacgccatgg ctatgggagt ggcttccgtt     600
tctcgagagt cgtgcgagaa cctgctcact aagggaggtg ctgacggaga gggaatgggc     660
cgagctatca ccattgttgt cggaggcgcc cgagagtccc tcgatgctct gcctcacact     720
atgcgactgg tcctcaagcg acgaaagggt ttcatcaagc tggccattcg aaccggagct     780
gacctcgttc ccgtcctggc cttcggcgag aacgacctct acgagcaggt gcgatctgat     840
cagcaccctc tgatctacaa ggtccagatg ctcgtgaagc gattcctggg ttttaccgtg     900
cccctgttcc atgctcgagg aatttttaac tacgacgttg gcctcatgcc ttaccgacga     960
cccctgaaca tcgtggttgg tcgacccatt caggtcgtgc gacagcagga ccgagataag    1020
atcgacgatg agtacattga ccgactccac gccgagtacg tccgagagct cgagtccctg    1080
tgggaccagt ggaaggatgt ttacgccaag gaccgaatct ctgagctgga gattgtcgct    1140
taa                                                                   1143

<210> SEQ ID NO 15
<211> LENGTH: 437
<212> TYPE: PRT
<213> ORGANISM: Claviceps purpurea

<400> SEQUENCE: 15

Met Ala Ala Val Gln Val Ala Arg Pro Val Pro Pro His His His Asp
1               5                   10                  15

Gly Ala Gly Arg Glu His Lys Gly Glu Arg Ala His Ser Pro Glu Arg
            20                  25                  30

Gly Glu Lys Thr Val His Asn Gly Tyr Gly Leu Ala Glu Thr His Glu
        35                  40                  45

Pro Leu Glu Leu Asn Gly Ser Ala Val Gln Asp Gly Lys His Asp Ser
    50                  55                  60

Asp Glu Thr Ile Thr Asn Gly Asp Tyr Ser Pro Tyr Pro Glu Leu Asp
65                  70                  75                  80

Cys Gly Lys Glu Arg Ala Ala His Glu Lys Glu Ala Trp Thr Ala Gly
                85                  90                  95
```

-continued

```
Gly Val Arg Phe Ala Pro Leu Arg Val Pro Phe Lys Arg Arg Met Gln
            100                 105                 110

Thr Ala Ala Val Leu Phe His Cys Met Ser Ile Ile Leu Ile Ser Ser
        115                 120                 125

Cys Phe Trp Phe Ser Leu Ala Asn Pro Ile Thr Trp Pro Ile Leu Val
    130                 135                 140

Pro Tyr Leu Val His Leu Ser Leu Ser Asn Ala Ser Thr Asp Gly Lys
145                 150                 155                 160

Leu Ser Tyr Arg Ser Glu Trp Leu Arg Ser Leu Pro Leu Trp Arg Leu
                165                 170                 175

Phe Ala Gly Tyr Phe Pro Ala Lys Leu His Lys Thr Phe Asp Leu Pro
            180                 185                 190

Pro Asn Arg Lys Tyr Ile Phe Gly Tyr His Pro His Gly Ile Ile Ser
        195                 200                 205

His Gly Ala Trp Cys Ala Phe Ala Thr Asn Ala Leu Gly Phe Val Glu
    210                 215                 220

Lys Phe Pro Gly Ile Thr Asn Ser Leu Leu Thr Leu Asp Ser Asn Phe
225                 230                 235                 240

Arg Val Pro Phe Tyr Arg Asp Trp Ile Leu Ala Met Gly Ile Arg Ser
                245                 250                 255

Val Ser Arg Glu Ser Ile Arg Asn Ile Leu Ser Lys Gly Gly Pro Asp
            260                 265                 270

Ser Asn Gly Gln Gly Arg Ala Val Thr Ile Val Ile Gly Gly Ala Arg
        275                 280                 285

Glu Ser Leu Glu Ala Gln Pro Gly Thr Leu Arg Leu Ile Leu Gln Gly
    290                 295                 300

Arg Lys Gly Phe Ile Lys Val Ala Leu Arg Ala Gly Ala Asp Leu Val
305                 310                 315                 320

Pro Val Ile Gly Phe Gly Glu Asn Asp Leu Tyr Asp Gln Leu Ser Pro
                325                 330                 335

Lys Thr His Pro Leu Val His Lys Ile Gln Met Phe Phe Leu Lys Val
            340                 345                 350

Phe Lys Phe Thr Ile Pro Ala Leu His Gly Arg Gly Leu Leu Asn Tyr
        355                 360                 365

Asp Val Gly Leu Leu Pro Tyr Arg Arg Ala Val Asn Ile Val Val Gly
    370                 375                 380

Arg Pro Ile Gln Ile Asp Glu Thr Tyr Gly Glu Gln Pro Pro Gln Glu
385                 390                 395                 400

Val Ile Asp Arg Tyr His Glu Leu Tyr Val Gln Glu Val Glu Arg Leu
                405                 410                 415

Tyr Ala Ala Tyr Lys Glu Gln Phe Ser Asn Gly Lys Lys Thr Pro Glu
            420                 425                 430

Leu Gln Ile Leu Ser
        435
```

```
<210> SEQ ID NO 16
<211> LENGTH: 1314
<212> TYPE: DNA
<213> ORGANISM: Claviceps purpurea

<400> SEQUENCE: 16
atggctgctg ttcaggttgc ccgacccgtt cccccccacc accacgatgg cgctggccga      60
gagcacaagg gagagcgagc ccattcccct gagcgaggag agaagaccgt ccacaacggc     120
tacggtctgg ccgagactca tgagcccctg gagctcaacg gttctgctgt gcaggacgga     180
```

```
aagcacgact cggatgagac catcactaac ggtgactact ctccctaccc tgagctcgat    240
tgcggaaagg agcgagccgc tcatgagaag gaggcttgga ccgctggagg tgtgcgattc    300
gctcctctgc gagttccttt aagcgacga atgcagactg ccgctgtcct cttccactgc    360
atgtccatca ttctgatttc ctcttgtttc tggttttctc tcgccaaccc catcacctgg    420
cctattctcg ttccctacct ggtccacctg tcgctctcca acgcttctac tgacggcaag    480
ctctcctacc gatctgagtg gctgcgatcc ctgcctctct ggcgactgtt cgccggttac    540
tttcccgcta agctccacaa gaccttcgat ctgcccccta accgaaagta catctttggt    600 taccacccc atggaatcat ttcccatggc gcctggtgtg ccttcgctac caacgctctg    660
ggcttcgttg agaagtttcc tggtattacc aactcgctgc tcactctcga ctccaacttc    720
cgagtgccct ttaccgaga ttggatcctg ccatgggca ttcgatctgt ttcgcgagag    780
tctatccgaa acattctctc gaagggagga cctgactcca acggacaggg ccgagctgtg    840
accatcgtta ttggtggagc ccgagagtct ctggaggctc agcccggaac tctgcgactc    900
attctgcagg gccgaaaggg cttcattaag gtggctctcc gagctggagc tgacctggtt    960
cccgtcatcg gtttcggaga gaacgacctc tacgatcagc tgtcccctaa gacccacccc   1020
ctcgttcata agatccagat gttctttctg aaggtcttca gtttactat tcctgctctg   1080 cacggacgag gtctgctcaa ctacgacgtc ggtctgctcc cttaccgacg agctgtgaac   1140
atcgtcgtgg acgacccat ccagattgac gagacctacg gcgagcagcc ccctcaggag   1200
gtcatcgatc gataccacga gctctacgtc caggaggtgg agcgactgta cgccgcttac   1260
aaggagcagt tctcgaacgg aaagaagacc cccgagctcc agatcctgtc ctaa          1314
```

<210> SEQ ID NO 17
<211> LENGTH: 351
<212> TYPE: PRT
<213> ORGANISM: Aurantiochytrium limacinum

<400> SEQUENCE: 17

```
Met Leu Ala Trp Met Pro Val Leu Ile Ala Leu Pro Arg Arg Lys Gln
1               5                   10                  15

Thr Ala Val Val Leu Leu Phe Val Met Leu Leu Pro Met Ile Met Val
                20                  25                  30

Val Tyr Ser Trp Thr Leu Ile Leu Leu Ile Phe Pro Leu Thr Thr Leu
            35                  40                  45

Pro Thr Leu Ser Tyr Leu Ile Trp Ile Met Tyr Ile Asp Lys Ser His
        50                  55                  60

Glu Thr Gly Lys Arg Lys Pro Phe Met Arg Tyr Trp Lys Met Trp Arg
65                  70                  75                  80

His Phe Ala Asn Tyr Phe Pro Leu Arg Leu Ile Arg Thr Thr Pro Leu
                85                  90                  95

Asp Pro Arg Arg Lys Tyr Val Phe Cys Tyr His Pro His Gly Ile Ile
            100                 105                 110

Ser Leu Gly Ala Phe Gly Asn Phe Ala Thr Asp Ser Thr Gly Phe Ser
        115                 120                 125

Arg Lys Phe Pro Gly Ile Asp Leu Arg Leu Leu Thr Leu Gln Ile Asn
    130                 135                 140

Phe Tyr Cys Pro Ile Ile Arg Glu Leu Leu Leu Tyr Met Gly Leu Cys
145                 150                 155                 160

Ser Ala Ala Lys Lys Ser Cys Asn Gln Ile Leu Gln Arg Gly Pro Gly
                165                 170                 175
```

Ser Ala Ile Met Leu Val Val Gly Gly Ala Ala Glu Ser Leu Asp Ser
            180                 185                 190

Gln Pro Gly Thr Tyr Arg Leu Thr Leu Gly Arg Lys Gly Phe Val Arg
        195                 200                 205

Val Ala Leu Asp Asn Gly Ala Asp Leu Val Pro Val Leu Gly Phe Gly
    210                 215                 220

Glu Asn Asp Val Phe Asp Thr Val Tyr Leu Pro Pro Asn Ser Trp Ala
225                 230                 235                 240

Arg Asn Val Gln Glu Phe Val Arg Lys Lys Leu Gly Phe Ala Thr Pro
                245                 250                 255

Ile Phe Ser Gly Arg Gly Ile Phe Gln Tyr Asn Met Gly Leu Met Pro
            260                 265                 270

His Arg Lys Pro Ile Ile Val Val Gly Lys Pro Ile Lys Ile Pro
        275                 280                 285

Lys Ile Pro Asp Glu Leu Lys Gly Arg Ala Leu Ser Thr Thr Ala Glu
290                 295                 300

Gly Val Ala Leu Val Asp Lys Tyr His Glu Lys Tyr Val Arg Ala Leu
305                 310                 315                 320

Arg Glu Leu Trp Asn Leu Tyr Lys Glu Glu Tyr Ala Thr Glu Pro Lys
                325                 330                 335

Ala Ala Tyr Leu Glu Pro Asn Ser Ile Arg Lys Asn Gln Asn Val
            340                 345                 350

<210> SEQ ID NO 18
<211> LENGTH: 1056
<212> TYPE: DNA
<213> ORGANISM: Aurantiochytrium limacinum

<400> SEQUENCE: 18

```
atgctcgcct ggatgcctgt cctcattgcc ctccccgac gaaagcagac cgctgttgtt      60
ctcctgtttg tgatgctcct ccctatgatc atggtcgtgt actcctggac cctgatcctg     120
ctcattttcc ccctcaccac tctgcctact ctctcctacc tgatctggat tatgtacatt     180
gacaagtctc acgagaccgg aaagcgaaag ccctttatgc gatactggaa gatgtggcga     240
catttcgcca actactttcc tctccgactg atccgaacca ctccctggaa ccctcgacga     300
aagtacgtgt ctgctaccca ccccatggc atcatttccc tcggagcctt cggcaacttt     360
gctaccgact cgactggctt ctcccgaaag tttcccggta tcgatctgcg actgctcacc     420
ctccagatta acttctactg tcctatcatt cgagagctgc tcctgtacat gggtctgtgc     480
tctgccgcta agaagtcgtg taaccagatc ctccagcgag acccggctc tgctattatg     540
ctggttgtcg gcggtgccgc tgagtccctc gactctcagc ctggcaccta ccgactcact     600
ctgggtcgaa agggattcgt gcgagttgcc ctggacaacg gtgctgatct ggtccccgtg     660
ctcggtttcg gagagaacga cgtgtttgat accgtttacc tgcccccta ctcgtgggcc     720
cgaaacgtcc aggagttcgt gcgaaagaag ctcggattcg ctaccccat cttttccggc     780
cgaggtattt ttcagtacaa catgggtctg atgccccacc gaaagcctat cattgtggtt     840
gtcggaaagc ccatcaagat tcccaagatc cctgacgagc tgaagggacg agccctctct     900
accactgccg agggcgttgc tctggtcgat aagtaccatg agaagtacgt tcgagccctc     960
cgagagctgt ggaacctcta caaggaggag tacgctaccg agcccaaggc cgcttacctc    1020
gagcctaact cgattcgaaa gaaccagaac gtctaa                              1056
```

DIACYLGLYCEROL ACYLTRANSFERASE (DGA1) POLYNUCLEOTIDES, AND METHODS OF INCREASING YEAST CELL LIPID PRODUCTION BY OVEREXPRESSION OF HETEROLOGOUS DGA1

CROSS-REFERENCE TO RELATED APPLICATIONS

This application is a divisional of U.S. patent application Ser. No. 15/120,952, filed Aug. 23, 2016, which claims the benefit of PCT/EP2015/017227, filed Feb. 24, 2015, which claims priority to U.S. Provisional Patent Application No. 61/943,664, filed Feb. 24, 2014, which are incorporated herein by reference in their entireties for all purposes.

FIELD OF INVENTION

The field of the invention is genetic engineering of oleaginous and/or high-temperature-tolerant yeast. The overexpression in yeasts of polynucleotides encoding heterologous DGA1, e.g., taken from *Rhodosporidium toruloides, Lipomyces starkeyi, Aurantiochytrium limacinum, Aspergillus terreus*, or *Claviceps purpurea*, results in engineered strains of yeast cells, such as *Yarrowia lipolytica*, capable of efficiently producing lipids in high concentrations.

BACKGROUND OF THE INVENTION

Lipids have multiple industrial applications, including applications in the cosmetic and food industries, as well as serving as precursors for biodiesel and various biochemicals. Microbial lipids are produced by many oleaginous organisms, including the yeast *Y. lipolytica* (Beopoulos A, et al. *Y. lipolytica* as a model for bio-oil production. *Prog Lipid Res.* 2009 November; 48(6):375-87). Lipid yield in oleaginous organisms can be increased by up-regulating and/or down-regulating or deleting genes implicated in the lipid pathway (Tai M, et al. Engineering the push and pull of lipid biosynthesis in oleaginous yeast *Y. lipolytica* for biofuel production. *Metab Eng.* 2013 January; 15: 1-9; Beopoulos A, et al. Control of lipid accumulation in the yeast *Y. lipolytica. Appl Environ Microbiol.* 2008 December; 74(24): 7779-7789). For example, it was reported that up-regulation of native *Y. lipolytica* DGA1 significantly increased lipid yield and productivity (Tai M. et al. *Metab Eng.* 2013 January; 15:1-9). DGA1 (diacylglycerol acyltransferase) is one of the key components of the lipid pathway involved in the final step of synthesis of triacylglycerol (TAG), which is a major component of lipids (Beopoulos A, et al. Identification and characterization of DGA2, an acyltransferase of the DGAT1 acyl-CoA:diacylglycerol acyltransferase family in the oleaginous yeast *Y. lipolytica*. New insights into the storage lipid metabolism of oleaginous yeasts. *Appl Microbiol Biotechnol.* 2012 February; 93(4): 1523-37). The Tai 2013 publication disclosed data suggesting that DGA1 efficiency may be a significant factor that is critical for high level of lipid accumulation in oleaginous organisms. Besides manipulation of homologous genes, heterologous genes also may be introduced into the host genome and have significant effect on lipid production and composition (Courchesne N M, et al. Enhancement of lipid production using biochemical, genetic and transcription factor engineering approaches. *J Biotechnol.* 2009 Apr. 20 141(1-2):31-41). Further, other oleaginous yeast, such as *R. toruloides* and *L. starkeyi*, are able to accumulate significantly more lipids compared to the wild-type *Y. lipolytica* strains (Sitepu I R, et al. Manipulation of culture conditions alters lipid content and fatty acid profiles of a wide variety of known and new oleaginous yeast species. *Bioresour Technol.* 2013 September; 144:360-9; Liang M H. et al. Advancing oleaginous microorganisms to produce lipid via metabolic engineering technology. *Prog Lipid Res.* 2013 October; 52(4):395-408; Ageitos J M, et al. Oily yeasts as oleaginous cell factories. *Appl Microbiol Biotechnol.* 2011 May; 90(4):1219-27; Papanikolaou S, et al. Lipids of oleaginous yeasts. Part I: Biochemistry of single cell oil production. *European Journal of Lipid Science and Technology* 2011 June; 113(8):1031-1051; Pan L X, et al. Isolation of Oleaginous Yeasts, *Food Technol. Biotechnol.* 2009 47(2):215-220; Ratledge C, et al. The biochemistry and molecular biology of lipid accumulation in oleaginous microorganisms. *Adv Appl Microbiol.* 2002 51:1-51; Kaneko H, et al. Lipid composition of 30 species of yeast. *Lipids.* 1976 December; 11(12):837-44). Despite efforts to increase lipid yield in *Y. lipolytica* by overexpression of heterologous DGA1 from *Mortierella alpine*, no significant effect on lipid production levels has been reported (U.S. Pat. No. 7,198,937).

Remarkably, Applicants have solved the long-standing problem by overexpressing polynucleotides encoding DGA1 from highly oleaginous organisms. These polynucleotides, when introduced in yeast, such as *Y. lipolytica*, created engineered yeast strains capable of increased yields of lipids compared to strains overexpressing native *Y. lipolytica* DGA1.

SUMMARY OF INVENTION

The present invention relates to the overexpression of polynucleotides encoding DGA1 from highly oleaginous organisms, such as *Rhodosporidium toruloides. Lipomyces starkeyi. Aurantiochytrium limacinum, Aspergillus terreus*, and *Claviceps purpurea*, in yeast, such as *Y. lipolytica*. The DGA1 and encoded polypeptide are useful in manipulating the production of commercially useful oils, triacylglyerols, and lipids in microorganisms, particularly yeast. Specifically, the present invention relates to increasing production of lipids in an yeast, such as *Yarrowia lipolytica*, by introducing heterologous DGA1 polynucleotides. Overexpression in *Y. lipolytica* of several DGA1 genes from the most efficient lipid-producing organisms resulted in dramatic increases in *Y. lipolytica* lipid production when compared to overexpression of native DGA1 in *Y. lipolytica*.

One aspect of the invention relates to a method for producing a recombinant yeast cell, the method comprising the steps of:
  a) introducing into a yeast cell a recombinant DNA construct comprising a heterologous polynucleotide selected from the group consisting of:
    i) a nucleic acid molecule comprising the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a complement thereof; and
    ii) a nucleic acid molecule having at least 80% sequence identity to the nucleotide sequence set forth in SEQ ID NO: 4, SEQ ID NO: 6, SEQ ID NO: 8. SEQ ID NO: 10, SEQ ID NO: 12, SEQ ID NO: 14, SEQ ID NO: 16, or SEQ ID NO: 18, or a complement thereof; and
  b) expressing a heterologous polypeptide selected from the group consisting of: i) amino acid sequence set forth in SEQ ID NO: 3, SEQ ID NO: 5, SEQ ID NO:

7, SEQ ID NO: 9, SEQ ID NO: 11, SEQ ID NO: 13, SEQ ID NO: 15, or SEQ ID NO: 17, or a biologically-active portion thereof; and ii) a polypeptide having at least 80% sequence identity to the amino acid sequence set forth in SEQ ID NO: 3, SEQ ID NO: 5. SEQ ID NO: 7, SEQ ID NO: 9, SEQ ID NO: 11. SEQ ID NO: 13, SEQ ID NO: 15, or SEQ ID NO: 17, or a biologically-active portion thereof; and c) cultivating the yeast cell under conditions for increasing lipid production.

In certain embodiments, said yeast cell is *Y. lipolytica* strain.

In certain embodiments, said polynucleotide is selected from the group consisting of a nucleic acid molecule having at least 95% sequence identity to the nucleotide sequence set forth in SEQ ID NO: 4. SEQ ID NO: 6, SEQ ID NO: 8, SEQ ID NO: 10, SEQ ID NO: 12, SEQ ID NO: 14, SEQ ID NO: 16, and SEQ ID NO: 18.

In certain embodiments, said polynucleotide is selected from the group consisting of SEQ ID NO: 6, SEQ ID NO: 8, and SEQ ID NO: 10.

In certain embodiments, said polypeptide is selected from the group consisting of a polypeptide having at least 95% sequence identity to the amino acid sequence set forth in SEQ ID NO: 3, SEQ ID NO: 5, SEQ ID NO: 7, SEQ ID NO: 9. SEQ ID NO: 11, SEQ ID NO: 13. SEQ ID NO: 15, and SEQ ID NO: 17.

In certain embodiments, said polypeptide is selected from the group consisting of SEQ ID NO: 5, SEQ ID NO: 7, and SEQ ID NO: 9.

Another aspect of the invention relates to an isolated host cell comprising a heterologous polynucleotide selected from the group consisting of:

a) a nucleic acid molecule comprising a nucleotide sequence set forth in SEQ ID NO: 4. SEQ ID NO: 6, SEQ ID NO: 8, SEQ ID NO: 10, SEQ ID NO: 12, SEQ ID NO: 14, SEQ ID NO: 16, or SEQ ID NO: 18, or a complement thereof, and b) a nucleic acid molecule comprising a nucleotide sequence having at least 80% sequence identity to the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a complement thereof.

In certain embodiments, said polynucleotide is selected from the group consisting of a nucleic acid molecule having at least 95% sequence identity to the nucleotide sequence set forth in SEQ ID NO: 4, SEQ ID NO: 6, SEQ ID NO: 8, SEQ ID NO: 10. SEQ ID NO: 12, SEQ ID NO: 14, SEQ ID NO: 16, and SEQ ID NO: 18.

In certain embodiments, said polynucleotide is selected from the group consisting of SEQ ID NO: 6, SEQ ID NO: 8, and SEQ ID NO: 10.

In certain embodiments, said isolated host cell is a yeast or fungi.

In certain embodiments, said isolated host cell is yeast, and said yeast is oleaginous, high-temperature tolerant, or both.

In certain embodiments, said yeast is an oleaginous yeast cell, and said oleaginous yeast cell is selected from the group consisting of *Rhodosporidium toruloides, Rhodosporidium babjevae, Rhodosporidium paludigenum, Lipomyces starkeyi, Lipomyces tetrasporus, Lipomyces lipofer, Cryptococcus curvatus, Cryptococcus albidus, Cryptococcus terreus, Cryptococcus ramirezgomezianus, Cryptococcus wieringae, Rhodotorula glutinis, Rhodotorula mucilaginosa, Trichosporon cutaneum, Cunninghamella echinulata, Mortierella isabellina, Trichosporon fermentans, Cunninghamella japonica, Aurantiochytrium limacinum, Rhizopus arrhizus, Aspergillus terreus, Claviceps purpurea, Leucosporidiella creatminivora, Tremella enchepala, Yarrowia lipolytica,* and *Prototheca zopfii.*

In certain embodiments, said oleaginous yeast cell is *Yarrowia lipolytica.*

In certain embodiments, said isolated host cell is an oleaginous, high-temperature tolerant yeast cell, and said oleaginous, high-temperature tolerant yeast cell is *Arxula adeniovorans.*

In certain embodiments, said isolated host cell is a high-temperature tolerant yeast cell, and said high-temperature tolerant yeast cell is *Kluyveromyces marxianus.*

In certain embodiments, the present invention relates to a product produced by a modified host cell described herein.

In certain embodiments, the product is an oil, lipid, or triacylglycerol.

Another aspect of the invention relates to a method of increasing lipid content in a transformed host cell comprising:

a) providing a transformed host cell comprising:
   i. a heterologous polynucleotide selected from the group consisting of:
      1. a nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, or SEQ ID NO: 18, or a complement thereof, and
      2. a nucleotide acid molecule having at least 80% sequence identity to the nucleotide sequence set forth in SEQ ID NO: 4. SEQ ID NO: 6. SEQ ID NO: 8, SEQ ID NO: 10, SEQ ID NO: 12, SEQ ID NO: 14, SEQ ID NO: 16, or SEQ ID NO: 18, or a complement thereof:
   wherein said polynucleotide encodes a DGA1 polypeptide selected from the group consisting of: i) amino acid sequence set forth in SEQ ID NO: 3. SEQ ID NO: 5, SEQ ID NO: 7, SEQ ID NO: 9, SEQ ID NO: 11, SEQ ID NO: 13, SEQ ID NO: 15, or SEQ ID NO: 17, or a biologically-active portion thereof; and ii) a polypeptide having at least 80% sequence identity to the amino acid sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, or SEQ ID NO: 17, or a biologically-active portion thereof;

b) growing the cell of step (a) under conditions whereby the nucleic acid molecule encoding DGA1 polypeptide is expressed, resulting in the production of lipids; and c) recovering the lipids of step (b).

In certain embodiments, the host cell is *Y. lipolytica.*

In certain embodiments, said polynucleotide is selected from the group consisting of a nucleic acid molecule having at least 95% sequence identity to the nucleotide sequence set forth in SEQ ID NO: 4. SEQ ID NO: 6, SEQ ID NO: 8, SEQ ID NO: 10, SEQ ID NO: 12, SEQ ID NO: 14, SEQ ID NO: 16, and SEQ ID NO: 18.

In certain embodiments, the polynucleotide is selected from the group consisting of SEQ ID NO: 6, SEQ ID NO: 8, and SEQ ID NO: 10.

In certain embodiments the polypeptide is selected from the group consisting of a polypeptide having at least 95% sequence identity to the amino acid sequence set forth in SEQ ID NO: 3, SEQ ID NO: 5. SEQ ID NO: 7, SEQ ID NO: 9, SEQ ID NO: 11, SEQ ID NO: 13, SEQ ID NO: 15, and SEQ ID NO: 17.

In certain embodiments, the polypeptide is selected from the group consisting of SEQ ID NO: 5. SEQ ID NO: 7, and SEQ ID NO: 9.

In certain embodiments, the isolated host cell is grown in the presence of a substrate selected from the group consisting of glucose, ethanol, xylose, sucrose, starch, starch dextrin, glycerol, cellulose, and acetic acid.

In certain embodiments, the present invention relates to a product produced from the method of increasing lipid content in a transformed host cell.

In certain embodiments, the product is an oil, lipid, or triacylglycerol.

One skilled in the art will readily appreciate that the present invention is well adapted to carry out the objects and obtain the ends and advantages mentioned, as well as those inherent therein. The embodiments described herein are not intended as limitations on the scope of the invention.

These and other features, aspects, and advantages of the present invention will become better understood with reference to the following description, drawings, and claims.

BRIEF DESCRIPTION OF THE DRAWINGS

FIG. 1 shows expression construct pNC243 with NG66. The expression constructs for all other DGA1 genes were the same as pNC243 except for the DGA1 ORF. For each construct, 8 transformants were analyzed by lipid assay. The "parent" strain NS18 was done in duplicate and the results are shown with standard deviation. The lipid assay was performed as described in Example 4. The samples were analyzed after 72 hours of cell growth in lipid-production-inducing media in a 96-well plate. The results are shown in FIG. 2.

FIG. 1 shows expression construct pNC243 with NG66. The expression construct for NG15 gene (pNC201) was the same as pNC243 except for the DGA1 ORF. The NS249 strain was done in duplicate and the results are shown with standard deviation. The lipid assay was performed as described in Example 4. The samples were analyzed after 72 hours of cell growth in lipid-production-inducing media in shake flasks. The glucose was measured in the same samples by a standard HPLC method. The results are shown in FIG. 3.

DETAILED DESCRIPTION OF THE INVENTION

Figure 1:
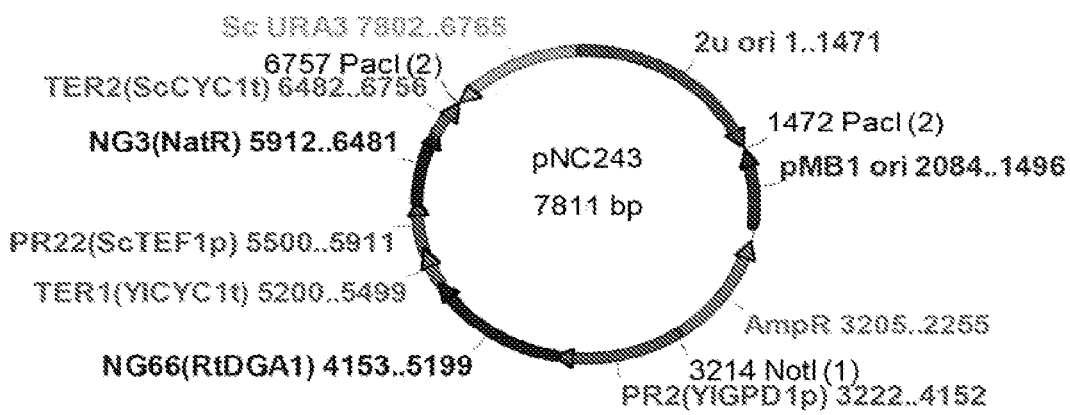
FIG. 1 shows a map of the pNC243 construct used to overexpress NG66 gene in *Y. lipolytica* strain NS18 (obtained from ARS Culture Collection, NRRL #YB 392). Vector pNC243 was linearized by PacI/NotI restriction digest before transformation. "2u ori" denotes the *S. cerevisiae* origin of replication from 2µ circle plasmid; "pMB1 ori" denotes the *E. coli* pMB1 origin of replication from pBR322 plasmid; "AmpR" denotes the bla gene used as marker for selection with ampicillin; "PR2" denotes the *Y. lipolytica* GPD1 promoter −931 to −1; "NG66" denotes the native *Rhodosporidium toruloides* DGA1 cDNA synthesized by GenScript: "TER1" denotes the *Y. lipolytica* CYC1 terminator 300 bp after stop; "PR22" denotes the *S. cerevisiae* TEF1 promoter −412 to −1; "NG3" denotes the *Streptomyces noursei* Nat1 gene used as marker for selection with nourseothricin: "TER2" denotes the *S. cerevisiae* CYC1 terminator 275 bp after stop; and "Sc URA3" denotes the *S. cerevisiae* URA3 auxotrophic marker for selection in yeast.

The definitions and/or methods provided herein guide those of ordinary skill in the art in the practice of the present invention. Except where otherwise stated, terms are to be understood according to conventional usage by those of ordinary skill in the relevant art. To the extent to which any of the definitions and/or methods is found to be inconsistent with any of the definitions and/or methods provided in any patent or non-patent reference incorporated herein or in any reference found elsewhere, it is understood that the said definition and/or method which has been expressly provided/adopted in this application will be used herein. The singular terms "a," "an," and "the" include plural referents unless context clearly indicates otherwise. Similarly, the word "or" is intended to include "and" unless the context clearly indicates otherwise. Hence, "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

The present invention relates to overexpressing polynucleotides encoding DGA1 derived from *Rhodosporidium toruloides, Lipomyces starkeyi, Aurantiochytrium limacinum, Aspergillus terreus*, or *Claviceps purpurea*, and corresponding polypeptides derived therefrom, in host cells, such as yeast and fungi. The yeast host cells are characterized in that they are oleaginous, high-temperature tolerant, or both. Described herein are engineered recombinant host cells of *Yarrowia lipolytica* comprising a heterologous DGA1 polynucleotide that encodes a DGA1 protein, or functionally active portions thereof, having the capability of increasing lipid production and possessing the characteristic of enhanced glucose efficiency. Any strains available of the host cells, e.g., *Y. lipolytica*, may be used in the present methods. Said recombinant host cells may be propagated to produce commercial quantities of lipids.

In the context of the present application, a number of terms used throughout the specification have the indicated meanings unless expressly indicated to have a different meaning.

As used herein, a "biologically active portion" may refer to a fragment of DGA1 having biological activity for converting acyl-CoA and 1,2-diacylglycerol to TAG and CoA in a yeast. Biologically active portions of a DGA1 include peptides or polypeptides comprising amino acid sequences sufficiently identical to or derived from the amino acid sequence of the DGA1 protein, e.g., the amino acid sequence as set forth in SEQ ID NOs: 3, 5, 7, 9, 11, 13, 15, or 17, which include fewer amino acids than the full length DGA1, and exhibit at least one activity of a DGA1 protein. Typically, biologically active portions comprise a domain or motif having the catalytic activity of converting acyl-CoA and 1,2-diacylglycerol to TAG and CoA. A biologically active portion of a DGA1 protein can be a polypeptide which is, for example, 278 amino acids in length.

The DGA1 may have an amino acid sequence set forth in SEQ ID NO: 3, 5, 7, 9, 11, 13, 15, or 17. In other embodiments, the DGA1 is substantially identical to SEQ ID NO: 3, 5, 7, 9, 11, 13, 15, or 17, and retains the functional activity of the protein of SEQ ID NO: 3, 5, 7, 9, 11, 13, 15, or 17, yet differs in amino acid sequence due to natural allelic variation or mutagenesis. In another embodiment, the DGA1 protein comprises an amino acid sequence at least about 80%, 82%, 84%, 85%, 87%, 88%, 90%, 92%, 95%, 96%, 97%, 98%, 99%, 99.1%, 99.2%, 99.3%, 99.4%, 99.5%, 99.6%, 99.7%, 99.8%, 99.9% or more identical to SEQ ID NO: 1, 3, 5, 7, 9, 11, 13, 15, or 17.

The DGA1 polypeptides may comprise conservative substitutions, deletions, or insertions while still maintaining functional DGA1 activity. Conservative substitution tables are well known in the art (see, for example, Creighton (1984) Proteins. W.H. Freeman and Company (Eds.) and Table 3 below).

TABLE 3

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu; Val | | |

Amino acid substitutions, deletions and/or insertions may readily be made using peptide synthetic techniques well known in the art, such as solid phase peptide synthesis and/or any other synthetic techniques, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis or other site-directed mutagenesis protocols.

To determine the percent identity of two amino acid sequences or of two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences can be determined using the Needleman and Wunsch (J. Mol. Biol. 48:444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences can be determined using the GAP program in the GCG software package (available at http://www.gcg.com), using a NWSgapdna.CMP matrix and a gap weight of 40, 50, 60. 70, or 80 and a length weight of 1, 2, 3, 4, 5, or 6. In another embodiment, the percent identity between two amino acid or nucleotide sequences can be determined using the algorithm of E. Meyers and W. Miller (Comput. Appl. Biosci. 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'→3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules: while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

As used herein, "DGA1" means a diacylglycerol acyltransferase type 2 (DGAT2). DGA1 is an integral membrane protein that catalyzes the final enzymatic step in oil biosynthesis and the production of triacylglycerols in plants, fungi and mammals. The DGA1 may play a key role in altering the quantity of long-chain polyunsaturated fatty acids produced in oils of oleaginous organisms. DGA1 is related to the acyl-coenzyme A:cholesterol acyltransferase ("ACAT"). This enzyme is responsible for transferring an acyl group from acyl-coenzyme-A to the sn-3 position of 1,2-diacylglycerol ("DAG") to form triacylglycerol ("TAG") (thereby involved in the terminal step of TAG biosynthesis). DGA1 is associated with membrane and lipid body fractions in plants and fungi, particularly, in oilseeds where it contributes to the storage of carbon used as energy reserves. TAG is believed to be an important chemical for storage of energy in cells. DGA1 is known to regulate TAG structure and direct TAG synthesis.

The DGA1 polynucleotide and polypeptide sequences may be derived from highly oleaginous organisms having very high, native levels of lipid accumulation. (Sitepu et al., 2013; Liang et al., 2013; Ageitos et al., 2011; Papanikolaou et al., 2011; Pan et al., 2009; Ratledge et al., 2002; Kaneko et al., 1976). The list of organisms with reported lipid content about 50% and above are shown in Table 1. *R. toruloides* and *L. starkeyi* have the highest lipid content. Among the organisms in the Table 1, only five had publicly accessible sequence for DGA1 (bolded in the Table 1). DGA1 from five selected donors, *R. toruloides, L. starkeyi, A. limacinum, A. terreus*, and *C. purpurea*, were used.

TABLE 1

List of oleaginous fungi with reported lipid content about 50% and above (*Sitepu et al.*, 2013; *Liang et al.*, 2013; *Ageitos et al.*, 2011; *Papanikolaou et al.*, 2011; *Pan et al.*, 2009; *Ratledge et al.*, 2002; *Kaneko et al.*, 1977). Organisms with publicly accessible sequence for DGA1 gene are in bold.
Fungi with reported high lipid content

Rhodosporidium toruloides
Rhodosporidium babjevae
Rhodosporidium paludigenum
Lipomyces starkeyi
Lipomyces tetrasporus
Lipomyces lipofer
Cryptococcus curvatus
Cryptococcus albidus
Cryptococcus terreus
Cryptococcus ramirezgomezianus
Cryptococcus wieringae
Rhodotorula glutinis
Rhodotorula mucilaginosa
Trichosporon cutaneum
Cunninghamella echinulata
Mortierella isabellina
Trichosporon fermentans
Cunninghamella japonica
Aurantiochytrium limacinum
Rhizopus arrhizus
Aspergillus terreus
Claviceps purpurea
Leucosporidiella creatinivora
Tremella enchepala
Prototheca zopfii The term "domain", as used herein, refers to a set of amino acids conserved at specific positions along an alignment of sequences of evolutionarily related proteins. While amino acids at other positions can vary between homologues, amino acids that are highly conserved at specific positions indicate amino acids which are likely to be essential in the structure, stability or function of a protein. Identified by their high degree of conservation in aligned sequences of a family of protein homologues, they can be used as identifiers to determine if any polypeptide in question belongs to a previously identified polypeptide family.

The term "gene", as used herein, may encompass genomic sequences of the DGA1 which contain introns, particularly polynucleotide sequence encoding polypeptide sequence of the DGA1 involved in the catalytic activity of converting acyl-CoA and 1,2-diacylglycerol to TAG and CoA. The term further encompasses synthetic nucleic acids that did not derive from genomic sequence. In certain embodiments, the DGA1 genes lack introns, as they are synthesized based on the known DNA sequence of cDNA and protein sequence. In other embodiments, the DGA1 genes are synthesized, non-native cDNA wherein the codons have been optimized for expression in *Y. lipolytica* based on codon usage. The term can further include nucleic acid molecules comprising upstream, downstream, and/or intron nucleotide sequences. Genomic data for highly oleaginous organisms may be obtained from *R. toruloides* (Kumar S, et al. Genome sequence of the oleaginous red yeast *Rhodosporidium toruloides* MTCC 457. *Eukaryot Cell.* 2012 August: 11(8): 1083-4) and *L. starkeyi* (http://genome.jgi-psf.org/). DGA1 sequences may be identified based on homology to *Y. lipolytica* DGA1 using BLAST or genes annotated as "diacylglycerol acytransferase"

The term "heterologous", as used herein, refers to a DGA1 polynucleotide or polypeptide which is different from the host cell in which the DGA1 polynucleotide is introduced or polypeptide is produced. For example, an isolated host cell of the present invention is generated by introducing DGA1 polynucleotide from one genus into a host cell which has a different genus from the DGA1 polynucleotide. The DGA1 polynucleotide may be synthetic or from a different species, so long as the polynucleotide is non-native to the host cell.

The term "host cell", as used herein, includes any cell type which is susceptible to transformation, transfection, transduction, expression and the like with a nucleic acid construct or expression vector comprising and/or consisting of a heterologous polynucleotide of the present invention. Suitable host cell includes fungi, plants, and yeast cells. The yeast cells may have the characteristics of being oleaginous, high-temperature tolerant, or both. In certain embodiments, the host cell may comprise *R. toruloides, R. babjevae, Rhodosporidium paludigenum, L. starkeyi, L. tetrasporus, L. lipofer, C. curvatus, C. albidus, C. terreus, C. ramirezgomezianus, C. wieringae, R. glutinis, R. mucilaginosa, T. cutaneum, C. echinulata, M. isabellina, T. fermentans, C. japonica, A. limacinum, R. arrhizus, A. terreus, C. purpurea, L. creatinivora, T. enchepala, Y. lipolytica*, or *P. zopfii*. In certain embodiments, the yeast cell is any strain of *Y. lipolytica*. In preferred embodiments, the yeast cell is *Y. lipolytica* strain NS18. A recombinant *Y. lipolytica* host cell of the present invention is suitable for use in the manufacture of lipids. The recombinant *Y. lipolytica* host cell may further be characterized by enhanced glucose efficiency and increased production of lipids, oils, and TAGs for commercial use.

The term "homologues", as used herein, refers to a protein encompass peptides, oligopeptides, polypeptides, proteins and enzymes having amino acid substitutions, deletions and/or insertions relative to the unmodified protein in question and having similar biological and functional activity as the unmodified protein from which they are derived.

"Isolated" means altered "by the hand of man" from the natural state. If a composition or substance occurs in nature, it has been "isolated" if it has been changed or removed from its original environment, or both. For example, a polynucleotide or a polypeptide naturally present in a living yeast is not "isolated," but the same polynucleotide or polypeptide separated from the coexisting materials of its natural state is "isolated", as the term is employed herein.

The term "motif", as used herein, refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318). Prosite (Bucher and Bairoch (1994). A generalized profile syntax for biomolecular sequences motifs and its function in automatic sequence interpretation. (In) ISMB-94; Proceedings 2nd International Conference on Intelligent Systems for Molecular Biology. Altman R, Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: The Proteomics Server for In-Depth Protein Knowledge and Analysis, Nucleic Acids Res. 31:3784-3788(2003)). Domains or motifs may also be identified using routine techniques, such as by sequence alignment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene."

The term "operably linked" generally denotes herein a configuration in which a control sequence is placed at an appropriate position relative to the coding sequence of the polynucleotide sequence such that the control sequence directs the expression of the coding sequence of a polypeptide. For example, a promoter can be operably-linked with a coding sequence when it affects the expression of that coding sequence, i.e., that the coding sequence is under the transcriptional control of the promoter.

As used herein, a "polynucleotide" is a nucleotide sequence such as a full-length or nucleic acid fragment. A polynucleotide may be a polymer of RNA or DNA that is single- or double-stranded, that optionally contains synthetic, non-natural or altered nucleotide bases. A polynucleotide in the form of a polymer of DNA may comprise and/or consist of one or more segments of cDNA, genomic DNA, synthetic DNA, or mixtures/combination thereof. An isolated polynucleotide of the present invention may include at least one of 150 contiguous nucleotides (both upstream and downstream) derived from SEQ ID NO: 4, 6, 8, 10, 12, 14, 16, 18, or the complement of such sequences.

One embodiment of the present invention is a method of overexpressing a polynucleotide encoding a DGA1 polypeptide derived from *R. toruloides, L. starkeyi, A. limacinum, A. terreus, C. purpurea,* or *Y. lipolytica* comprising and/or consisting of nucleotide sequence as set forth in SEQ ID NO: 4, 6, 8, 10, 12, 14, 16, or 18. Correspondingly, the respective DGA1 polypeptide encoded by these nucleotide sequences shall possess amino acid sequence as set forth in SEQ ID NO: 3, 5, 7, 9, 11, 13, 15, or 17 and possess the catalytic ability of transferring an acyl group from acyl-coenzyme-A to the sn-3 position of 1,2-diacylglycerol ("DAG") to form triacylglycerol ("TAG") (thereby involved in the terminal step of TAG biosynthesis).

The DGA1 polynucleotides are capable of encoding a DGA1 polypeptide, or biologically-active portion thereof, and may comprise a nucleotide sequence which is at least about 80%, 82%, 84%, 85%, 87%, 88%, 90%, 92%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence set forth in SEQ ID NOs: 2, 4, 6, 8, 10, 12, 14, 16, or 18, or any complement thereof.

In accordance with the present invention, the isolated polynucleotide illustrated in SEQ ID NO: 4, 6, 8, 10, 12, 14, 16, or 18, or any complement thereof, of Table 2 can be obtained by PCR amplification of the conserved region of the genomic DNA using total RNA isolated from the yeast of *R. toruloides, L. starkeyi, A. limacinum, A. terreus, C. purpurea,* or *Y. lipolytica*. In certain embodiments, the DGA1 cDNA is synthesized by GenScript. In other embodiments, the cDNA codon of DGA1 is optimized for expression in *Y. lipolytica* and synthesized by GenScript. The polynucleotides provided by the present invention can also be used as preparatory materials for the rational modification or design of novel DGA1 enzymes with characteristics that enable the enzymes to perform better in demanding processes.

A "polypeptide" as used herein, is a single linear chain of amino acids bonded together by peptide bonds, and having usually a sequence greater than 277 amino acids in length. In certain embodiments the DGA1 polypeptide comprise the amino acid sequence as set forth in SEQ ID NO: 3, 5, 7, 9, 11, 13, 15, 17, or a biologically-active portion thereof. The DGA1 polypeptide, or biologically active portion thereof, possesses the catalytic ability of converting acyl-CoA and 1,2-diacylglycerol to TAG and CoA in the yeast.

The term "promoter", as used herein, refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. In certain embodiments, the promoter may be *Y. lipolytica* GPD1.

The term "synthetic" means chemically, enzymatically, or recombinantly engineered from the native or natural state. If a composition or substance occurs in nature, it is "synthetic" if it has been manufactured, engineered, or manipulated from its original environment, or both. For example, a polynucleotide or a polypeptide naturally present in a living yeast is not "synthetic." but the same polynucleotide or polypeptide chemically synthesized or recombinantly engineered is "synthetic", as the term is employed herein.

A "terminator" as used herein refers to a nucleic acid sequence that marks the end of a gene or transcription unit during transcription. The sequence mediates transcription termination by causing RNA polymerase to stop transcription and the newly synthesized mRNA to be released from the transcriptional complex. In certain embodiments, the terminator used in the present invention is derived from yeast. In certain embodiments, the terminator is *Y. lipolytica* or *S. cerevisiae* CYC1 terminator.

A "vector" generally refers to a replicon, such as plasmid, phage, cosmid, yeast or virus to which another nucleic acid segment may be operably inserted so as to bring about the replication or expression of the segment. The term "vector" is also intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced. Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, which may serve equivalent functions.

For the purposes of the invention, "transgenic", "transgene" or "recombinant" means with regard to, for example, a nucleic acid sequence, an expression cassette, DNA construct or a vector comprising and/or consisting of the polynucleotides or an organism transformed with the polynucleotides, expression cassettes or vectors according to the invention, all those constructions brought about by recombinant methods in which either: (a) the polynucleotides encoding proteins useful in the methods of the invention, or (b) genetic control sequence(s) which are operably linked with the polynucleotides according to the invention, for example a promoter or terminator, or (c) a) and b) are not located in their natural genetic environment or have been modified by recombinant methods.

The modification may take the form of, for example, a substitution, addition, deletion, inversion or insertion of one or more nucleotide residues. The natural genetic environment is understood as meaning the natural genomic or chromosomal locus in the original yeast or the presence in a genomic library. In the case of a genomic library, the natural genetic environment of the nucleic acid sequence is preferably retained, at least in part. The environment flanks the nucleic acid sequence at least on one side and has a sequence length of about 50 bp, preferably of about 500 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment or recombinant cloning.

A transgenic yeast for the purposes of the invention is thus understood as including those yeasts in which the polynucleotides used in the method of the invention are not at their natural locus in the genome of the said yeast, and thus it is possible for the polynucleotides to be expressed heterologously. However, as mentioned, transgenic also mean that, while the nucleic acids according to the invention or used in the inventive method are at their natural position in the genome of a yeast, the sequence has been modified with regard to the natural sequence, and/or that the regulatory sequences of the natural sequences have been modified. Transgenic is preferably understood as meaning the expression of the polynucleotides according to the invention at an unnatural locus in the genome, or heterologous expression of the polynucleotides in a non-native host cell.

In one embodiment, a recombinant DNA construct comprising and/or consisting of a polynucleotide having nucleotide sequence set forth in SEQ ID NO: 4, 6, 8, 10, 12, 14, 16, or 18, or any complement thereof, is disclosed, wherein the polynucleotide is expressible in a host cell, and is translatable to produce homologues or biologically-active portions of DGA1 protein in the yeast cells of *Y. lipoltica*. The procedure for amplifying and cloning the DGA1 from *R. toruloides, L. starkeyi, A. limacinum, A. terreus, C. purpurea,* or *Y. lipolytica* is further detailed in Example 1. The recombinant DNA construct may further comprise a promoter region operably-linked to enhance expression of the polynucleotide template. Under the transcriptional control of the specific promoter, the expression of the coding region within the recombinant DNA constructs containing DGA1 polynucleotides of the present can then be enhanced, leading to higher yield of the DGA1 protein. Methods for increasing expression of polynucleotides are provided in the definitions section, and include optimization of DGA1 codons, introduction or retention of intron sequences. The recombinant DNA construct may further comprise a terminator sequences for transcriptional regulation, such as *Y. lipolytica* or *S. cerevisiae* CYC1 terminator.

The term "transformation" or "introduction", as used herein, encompasses the transfer of an exogenous polynucleotide into a host cell, irrespective of the method used for transfer. Yeast capable of subsequent clonal propagation may be transformed with a genetic construct of the present invention and a whole yeast generated therefrom. The polynucleotide may be transiently or stably introduced into a host cell and may be maintained non-integrated, for example, as a plasmid. Alternatively, it may be integrated into the host genome. The resulting transformed yeast cell may then be propagated and used for commercial production of lipids.

The transfer of foreign genes into the genome of a yeast is called transformation.

Transformation of yeast species is now a fairly routine technique. Advantageously, any of several transformation methods may be used to introduce the gene of interest into a suitable ancestor cell. The methods described for the transformation of yeast cells may be utilized for transient or for stable transformation. Transformation methods include the use of liposomes, electroporation and chemicals which increase free DNA uptake, injection of the DNA directly into the yeast cell, particle gun bombardment, and transformation using viruses or pollen and microprojection.

Generally after transformation, yeast are selected for the presence of one or more markers which are encoded by yeast-expressible genes co-transferred with the gene of interest, following which the transformed material is regenerated into a whole yeast. To select transformed yeast, the yeast obtained in the transformation is subjected to selective conditions so that transformed yeasts can be distinguished from untransformed yeasts. For example, the transformed yeasts are grown on YPD plates using a suitable selection agent, such as nourseothricine (NAT). Subsequently, the transformants are screened for the ability to accumulate lipids by fluorescent staining lipid assay described in Example 3.

Following DNA transfer and transformation, putatively transformed yeast clones may also be evaluated, for instance using Southern analysis, for the presence of the gene of interest, copy number and/or genomic organization. Alternatively or additionally, expression levels of the newly introduced DNA may be monitored using Northern and/or Western analysis, both techniques being well known to persons having ordinary skill in the art.

The transformed yeast cell having enhanced glucose consumption efficiency and increased lipid production may be generated by a method comprising: (i) introducing and expressing in a yeast cell a DGA1 polypeptide-encoding nucleic acid or a genetic DNA construct comprising and/or consisting of a DGA1 polypeptide-encoding nucleic acid; and (ii) cultivating the yeast cell under conditions promoting growth and lipid production. In certain embodiments, exogenous fatty acids, glucose, ethanol, xylose, sucrose, starch, starch dextrin, glycerol, cellulose, or acetic acid are added during the cultivation step which may increase lipid production. Such fatty acids may include stearate, oleic acid, linoleic acid, γ-linoleic acid, dihomo-γ-linoleic acid, arachidonic acid, α-linoleic acid, stearidonic acid, eicosatetraenoic acid, eicosapenteaenoic acid, docosapentaenoic acid, eicosadienoic acid, or eicosatrienoic acid. In certain embodiments, the growth conditions are set forth in Example 4.

The term "increased expression" or "overexpression" as used herein, refers to any form of expression that is additional to the original wild-type expression level using native, *Y. lipolytica* DGA1 in its native, *Y. lipolytica* host. To further supplement the increased lipid yeasts in the host cells of the present invention, additional methods may be utilized to further increase expression of DGA1 proteins. Such methods are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution, or isolated promoters may be introduced into a yeast cell in the proper orientation and distance from the DGA1 polynucleotide of the present invention so as to control the expression of the DGA1 polynucleotide.

An intron sequence may also be added to the 5' untranslated region (UTR) or retained in the coding sequence of the full-length or partial coding sequence to increase the amount of the mature message that accumulates in the cytosol. Inclusion of a spliceable intron 3' or 5' to the transcription unit in the expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200).

The invention further provides a method of increasing lipid content in a transformed *Y. lipolytica* host cell, comprising and/or consisting of introducing and expressing in a yeast cell a polynucleotides having the nucleotide sequence set forth in SEQ ID NO: 4, 6, 8, 10, 12, 14, 16, or 18, or any complement thereof, capable of encoding a DGA1 polypeptide having the amino acid sequence set forth in SEQ ID NO: 3, 5, 7, 9, 11, 13, 15, or 17, or a biologically-active portion thereof. The transformed *Y. lipolytica* host cell may comprise a nucleotide sequence which is at least about 80%, 82%, 84%, 85%, 87%, 88%, 90%, 92%, 95%, 96%, 97%, 98%, 99%, 99.1%, 99.2%, 99.3%, 99.4%, 99.5%, 99.6%, 99.7%, 99.8%, 99.9% or more identical to the entire length of the nucleotide sequence set forth in SEQ ID NO: 4, 6, 8, 10, 12, 14, 16, or 18, or any complement thereof.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXEMPLIFICATION

Example 1: Identification of DGA1 Polynucleotides and Polypeptides

In order to test the hypothesis that DGA1 from highly oleaginous organisms can significantly increase lipid production in *Y. lipolytica*, organisms reported as having very high level of lipid accumulation were reviewed. (Sitepu et al., 2013; Liang et al., 2013; Ageitos et al., 2011; Papanikolaou et al., 2011; Pan et al., 2009; Ratledge et al., 2002; Kaneko et al., 1976). The list of organisms with reported lipid content about 50% and above are shown in Table 1. *R. toruloides* and *L. starkeyi* were reported to have the highest lipid content. Among the organisms in Table 1 only five had publicly accessible sequences for DGA1 gene (bolded in the Table 1). Therefore DGA1 genes from five selected donors (*R. toruloides, L. starkeyi, A. limacinum, A. terreus*, and *C. purpurea*) were expressed in *Y. lipolytica* under the control of a *Y. lipolytica* promoter and terminator. The DGA1 sequences used for overexpression in *Y. lipolytica*, including native *Y. lipolytica* DGA1 used as control, are described in Table 2. For *R. toruloides*, three versions of DGA1 gene were expressed in *Y. lipolytica:* 1) NG49—native *R. toruloides* DGA1 genes amplified from *R. toruloides* genomic DNA (SEQ ID NO: 2); 2) NG66—synthetic gene that contains *R. toruloides* DGA1 cDNA without introns (SEQ ID NO: 6); and 3) NG67—synthetic gene that contains *R. toruloides* DGA1 cDNA without introns codon optimized for expression in *Y. lipolytica* (SEQ ID NO: 8). For *L. starkeyi*, two versions of DGA1 gene were expressed in *Y. lipolytica:* 1) NG68—synthetic gene that contains *L. starkeyi* DGA1 cDNA without introns (SEQ ID NO: 10); and 2) NG69—synthetic gene that contains *L. starkeyi* DGA1 cDNA without introns codon optimized for expression in *Y. lipolytica* (SEQ ID NO: 12). For *A. limacinum, A. terreus*, and *C. purpurea*, synthetic DGA1 gene encoding cDNA without introns codon optimized for expression in *Y. lipolytica* was expressed in *Y. lipolytica* (SEQ ID NOs: 14, 16, and 18).

TABLE 2

Characterization of DGA1 genes and expression constructs used herein. The map of expression constructs used to express DGA1 genes is shown on FIG. 1 with NG66 as example. The constructs for all other DGA1 genes were the same except for the DGA1 ORF.

Gene ID: NG15
Expression construct ID: pNC201
Donor Organism: *Yarrowia lipolytica*
Gene: DGA1
Function: diacylglycerol acyltransferase
Sequence Source: KEGG database YALI0E32769g
DNA Source: Amplified from gDNA of *Y. lipolytica* NRRL YB-437

Protein Sequence (SEQ ID NO: 1):
MTIDSQYYKSRDKNDTAPKIAGIRYAPLSTPLLNRCETFSLVWHIFSIPTFLTIFML
CCAIPLLWPFVIAYVVYAVKDDSPSNGGVVKRYSPISRNFFIWKLFGRYFFITLHKT
VDLEPTHTYYPLDVQEYHLIAERYWPQNKYLRAIITTIEYFLPAFMKRSLSINEQEQ
PAERDPLLSPVSPSSPGSQPDKWINHDSRYSRGESSGSNGHASGSELNGNGNNGTTN
RRPLSSASAGSTASDSTLLNGSLNSYANQIIGENDPQLSPTKLKPTGRKYIFGYHPH
GIIGMGAFGGIATEGAGWSKLFPGIPVSLMTLTNNFRVPLYREYLMSLGVASVSKKS
CKALLKRNQSICIVVGGAQESLLARPGVMDLVLLKRKGFVRLGMEVGNVALVPIMAF
GENDLYDQVSNDKSSKLYRFQQFVKNFLGFTLPLMHARGVFNYDVGLVPYRRPVNIV
VGSPIDLPYLPHPTDEEVSEYHDRYIAELQRIYNEHKDEYFIDWTEEGKGAPEFRMI
E DNA Sequence (SEQ ID NO: 2):
ATGACTATCGACTCACAATACTACAAGTCGCGAGACAAAAACGACACGGCACCCAAA
ATCGCGGGAATCCGATATGCCCCGCTATCGACACCATTACTCAACCGATGTGAGACC
TTCTCTCTGGTCTGGCACATTTTCAGCATTCCCACTTTCCTCACAATTTTCATGCTA
TGCTGCGCAATTCCACTGCTCTGGCCATTTGTGATTGCGTATGTAGTGTACGCTGTT
AAAGACGACTCCCCGTCCAACGGAGGAGTGGTCAAGCGATACTCGCCTATTTCAAGA
AACTTCTTCATCTGGAAGCTCTTTGGCCGCTACTTCCCCATAACTCTGCACAAGACG
GTGGATCTGGAGCCCACGCACACATACTACCCTCTGGACGTCCAGGAGTATCACCTG
ATTGCTGAGAGATACTGGCCGCAGAACAAGTACCTCCGAGCAATCATCACCACCATC
GAGTACTTTCTGCCCGCCTTCATGAAACGGTCTCTTTCTATCAACGAGCAGGAGCAG
CCTGCCGAGCGAGATCCTCTCCTGTCTCCCGTTTCTCCCAGCTCTCCGGGTTCTCAA
CCTGACAAGTGGATTAACCACGACAGCAGATATAGCCGTGGAGAATCATCTGGCTCC
AACGGCCACGCCTCGGGCTCCGAACTTAACGGCAACGGCAACAATGGCACCACTAAC
CGACGACCTTTGTCGTCCGCCTCTGCTGGCTCCACTGCATCTGATTCCACGCTTCTT
AACGGGTCCCTCAACTCCTACGCCAACCAGATCATTGGCGAAAACGACCCACAGCTG
TCGCCCACAAAACTCAAGCCCACTGGCAGAAAATACATCTTCGGCTACCACCCCCAC
GGCATTATCGGCATGGGAGCCTTTGGTGGAATTGCCACCGAGGGAGCTGGATGGTCC
AAGCTCTTTGCGGGCATCCCTGTTTCTCTTATGACTCTCACCAACAACTTCCGAGTG
CCTCTCTACAGAGAGTACCTCATGAGTCTGGGAGTCGCTTCTGTCTCCAAGAAGTCC
TGCAAGGCCCTCCTCAAGCGAAACCAGTCTATCTGCATTGTCGTTGGTGGAGCACAG
GAAAGTCTTCTGGCCAGACCCGGTGTCATGGACCTGGTGCTACTCAAGCGAAAGGGT
TTTGTTCGACTTGGTATGGAGGTCGGAAATGTCGCCCTTGTTCCCATCATGGCCTTT
GGTGAGAACGACCTCTATGACCAGGTTAGCAACGACAAGTCGTCCAAGCTGTACCGA
TTCCAGCAGTTTGTCAAGAACTTCCTTGGATTCACCCTTCCTTTGATGCATGCCCGA
GGCGTCTTCAACTACGATGTCGGTCTTGTCCCCTACAGGCGACCCGTCAACATTGTG
GTTGGTTCCCCCATTGACTTGCCTTATCTCCCACACCCCACCGACGAAGAAGTGTCC
GAATACCACGACCGATACATCGCCGAGCTGCAGCGAATCTACAACGAGCACAAGGAT
GAATATTTCATCGATTGGACCGAGGAGGGCAAAGGAGCCCCAGAGTTCCGAATGATT
GAGTAA Gene ID: NG-49
Expression construct ID: pNC241
Donor Organism: *Rhodosporidium toruloides*
Gene: DGA1
Function: diacylglycerol acyltransferase
Sequence Source: GenBank BAH85840.1
DNA Source: Amplified from gDNA of *R. toruloides* NRRL Y-6987

Protein Sequence (SEQ ID NO: 3):
MGQQATPEELYTRSEISKIKFAPFGVPRSRRLQTFSVFAWTTALPILLGVFFLLCSF
PPLWPAVIAYLTWVFFIDQAPIHGGRAQSWLRKSRIWVWFAGYYPVSLIKSADLPPD
RKYVFGYHPHGVIGMGAIANFATDATGFSTLFPGLNPHLLTLQSNFKLPLYRELLLA
LGICSVSMKSCQNILRQGPGSALTIVVGGAAESLSAHPGTADLTLKRRKGFIKLAIR
QGADLVPVFSFGENDIFGQLRNERGTRLYKLQKRFQGVFGFTLPLFYGRGLFNYNVG
LMPYRHPIVSVVGRPISVEQKDHPTTADLEEVQARYIAELKRIWEEYKDAYAKSRTR
ELNIIA gDNA Sequence (SEQ ID NO: 4):
ATGGGCCAGCAGGCGACGCCCGAGGAGCTATACACACGCTCAGAGATCTCCAAGATC
AAGcaagtcgagccagctcttctcctcaccaccccacaacatacccgcagccacg
acagccctcccacagcacctgcagcctgctgaccagctcgagaacacccacagaTTC
GCACCCTTTGGCGTCCCGCGGTCGCGCCGGCTGCAGACCTTCTCCGTCTTTGCCTGG
ACGACGGCACTGCCCATCCTACTCGGCGTCTTCTTCCTCCTCTGgtgcgtcaggctt
ggcgtgatctgagggtagcgggcggatcatctgacctgcttcttcgctcaaCTCGT
TCCCACCGCTCTGGCCGGCTGTCATTGCCTACCTCACCTGGGTCTTTTTCATTGACC

TABLE 2-continued

Characterization of DGA1 genes and expression constructs used herein. The map of expression constructs used to express DGA1 genes is shown on FIG. 1 with NG66 as example. The constructs for all other DGA1 genes were the same except for the DGA1 ORF.

```
AGGCGCCGATTCACGGTGGACGGGCGCAGTCTTGGCTGCGGAAGAGTCGGATATGGG
TCTGGTTTGCAGGATACTATCCCGTCaggtgcgtcctcttttccaagcctgcgtctcg
aggcctcgctcacggccaactcgcccgaccggctaccctccgaactttccgtcaacAG
CTTGATCAAGgtcagtctgcgcgtctctcgacttcagtgctctgtgggaggagctgcg
ccattgggcccgacctgcggagggcctcaaaggacgatgccgctgacttcctttcct
ccgacagAGCGCCGACTTGCCGCCTGACCGGAAGTACGTCTTTGGCTACCACCCGCA
CGGCGTCATAGGCATGGGCGCCATCGCCAACTTCGCGACCGACGCAACCGGCTTCTC
GACACTCTTCCCCGGCTTGAACCCTCACCTCCTCACCCTCCAAAGCAACTTCAAGCT
CCCGCTCTACCGCGAGTTGCTGCTCGCTCTCGGCATATGCTCCGTCTCGATGAAGAG
CTGTCAGAACATTCTGCGACAAGGTgagcggtatgcgcaagacgggcggtcaagcgt
gaacgcagtgaacgagaagagctgaccttccgccttactccatccgtgcaggtCCTG
GCTCGGCTCTCACTATCGTCGTCGGTGGCGCCGCCGAGAGCTTGAGTGCGCATCCCG
GAACCGCCGATCTTACGCTCAAGCGACGAAAAGGCTTCATCAAACTCGCGATCCGGC
AAGGCGCCGACCTTGTGCCCGTCTTTTCGTTCGGCGAGAACGACgtgcgcacgctct
ccgagtctctaaaccggaagcgaatgctgaccgctgcccaattctctctccagATCT
TTGGCCAGCTGCGAAACGAGCGAGGAACGCGGCTGTACAAGTTGCAGAAGCGTTTCC
AAGGCGTGTTTGGCTTCACCCTCCgtacgtctcaccgcgccgtcttgccgaactgct
cgttcagtcgctcacgcagctttcactcgcgcagCTCTCTTCTACGGCCGGGGACTC
TTCAACTgtgcgctcgagttcaccgcttcgccaacagcgaggaatgcctccgagtac
agcccagctgacgcccatctcttctcatagACAACGTCGGATTGATGCCGTATCGC
CATCCGATCGTCTCTGTCggtgtgaacccgctctgtcgctcctacctgcgttcctta
ggctgacaccactcgcgtcaaacaGTCGGTCGACCAATCTCGGTAGAGCAGAAGGAC
CACCCGACCACGGCGGACCTCGAAGAAGTTCAGGCGCGGTATATCGCAGAACTCAAG
CGGtacgttccaagtcgtctgcctccgcttgccgcctcaaataagctgaggcgtgct
gaccgtatctgccgaaccgtacagcATCTGGGAAGAATACAAGGACGCCTACGCCAA
AAGTCGCACGCGGGAGCTCAATATTATCGCCTGA Gene ID: NG-66
Expression construct ID: pNC243
Donor Organism: Rhodosporidium toruloides
Gene: DGA1
Length: 348 (amino acid); 1047 (DNA)
Function: diacylglycerol acyltransferase
Sequence Source: GenBank BAH85840.1
DNA Source: Native cDNA synthesized by GenScript Protein Sequence (SEQ ID NO: 5):
MGQQATPEELYTRSEISKIKFAPFGVPRSRRLQTFSVFAWTTALPILLGVFFLLCSF
PPLWPAVIAYLTWVFFIDQAPIHGGRAQSWLRKSRIWVWFAGYYPVSLIKSADLPPD
RKYVFGYHPHGVIGMGAIANFATDATGFSTLFPGLNPHLLTLQSNFKLPLYRELLLA
LGICSVSMKSCQNILRQGPGSALTIVVGGAAESLSAHPGTADLTLKRRKGFIKLAIR
QGADLVPVFSFGENDIFGQLRNERGTRLYKLQKRFQGVFGFTLPLFYGRGLFNYNVG
LMPYRHPIVSVVGRPISVEQKDHPTTADLEEVQARYIAELKRIWEEYKDAYAKSRTR
ELNIIA DNA Sequence (SEQ ID NO: 6):
ATGGGCCAGCAGGCGACGCCCGAGGAGCTATACACACGCTCAGAGATCTCCAAGATC
AAGTTCGCACCCTTTGGCGTCCCGCGGTCGCGCCGGCTGCAGACCTTCTCCGTCTTT
GCCTGGACGACGGCACTGCCCATCCTACTCGGCGTCTTCTTCCTCCTCTGCTCGTTC
CCACCGCTCTGGCCGGCTGTCATTGCCTACCTCACCTGGGTCTTTTTCATTGACCAG
GCGCCGATTCACGGTGGACGGGCGCAGTCTTGGCTGCGGAAGAGTCGGATATGGGTC
TGGTTTGCAGGATACTATCCCGTCAGCTTGATCAAGAGCGCCGACTTGCCGCCTGAC
CGGAAGTACGTCTTTGGCTACCACCCGCACGGCGTCATAGGCATGGGCGCCATCGCC
AACTTCGCGACCGACGCAACCGGCTTCTCGACACTCTTCCCCGGCTTGAACCCTCAC
CTCCTCACCCTCCAAAGCAACTTCAAGCTCCCGCTCTACCGCGAGTTGCTGCTCGCT
CTCGGCATATGCTCCGTCTCGATGAAGAGCTGTCAGAACATTCTGCGACAAGGTCCT
GGCTCGGCTCTCACTATCGTCGTCGGTGGCGCCGCCGAGAGCTTGAGTGCGCATCCC
GGAACCGCCGATCTTACGCTCAAGCGACGAAAAGGCTTCATCAAACTCGCGATCCGG
CAAGGCGCCGACCTTGTGCCCGTCTTTTCGTTCGGCGAGAACGACATCTTTGGCCAG
CTGCGAAACGAGCGAGGAACGCGGCTGTACAAGTTGCAGAAGCGTTTCCAAGGCGTG
TTTGGCTTCACCCTCCCTCTCTTCTACGGCCGGGGACTCTTCAACTACAACGTCGGA
TTGATGCCGTATCGCCATCCGATCGTCTCTGTCGTCGGTCGACCAATCTCGGTAGAG
CAGAAGGACCACCCGACCACGGCGGACCTCGAAGAAGTTCAGGCGCGGTATATCGCA
GAACTCAAGCGGATCTGGGAAGAATACAAGGACGCCTACGCCAAAAGTCGCACGCGG
GAGCTCAATATTATCGCCTGA Gene ID: NG67
Expression construct ID: pNC244
Donor Organism: Rhodosporidium toruloides
Gene: DGA1
Length: 348 (amino acid); 1047 (DNA)
Function: diacylglycerol acyltransferase
Sequence Source: GenBank BAH85840.1
DNA Source: cDNA codon optimized for expression in Y. lipolytica and
synthesized by GenScript
```

TABLE 2-continued

Characterization of DGA1 genes and expression constructs used herein. The map of expression constructs used to express DGA1 genes is shown on FIG. 1 with NG66 as example. The constructs for all other DGA1 genes were the same except for the DGA1 ORF.

Protein Sequence (SEQ ID NO: 7):
MGQQATPEELYTRSEISKIKFAPFGVPRSRRLQTFSVFAWTTALPILLGVFFLLCSF
PPLWPAVIAYLTWVFFIDQAPIHGGRAQSWLRKSRIWVWFAGYYPVSLIKSADLPPD
RKYVFGYHPHGVIGMGAIANFATDATGFSTLFPGLNPHLLTLQSNFKLPLYRELLLA
LGICSVSMKSCQNILRQGPGSALTIVVGGAAESLSAHPGTADLTLKRRKGFIKLAIR
QGADLVPVFSFGENDIFGQLRNERGTRLYKLQKRFQGVFGFTLPLFYGRGLFNYNVG
LMPYRHPIVSVVGRPISVEQKDHPTTADLEEVQARYIAELKRIWEEYKDAYAKSRTR
ELNIIA DNA Sequence (SEQ ID NO: 8):
ATGGGACAGCAGGCTACCCCCGAGGAGCTCTACACCCGATCCGAGATTTCTAAGATT
AAGTTCGCCCCTTTTGGAGTGCCCCGATCCCGACGACTCCAGACCTTCTCCGTTTTT
GCCTGGACCACTGCTCTGCCCATTCTGCTCGGCGTCTTCTTTCTGCTCTGCTCTTTC
CCCCCTCTCTGGCCCGCCGTCATCGCTTACCTGACCTGGGTGTTCTTTATCGACCAG
GCCCCTATTCACGGCGGTCGAGCTCAGTCCTGGCTGCGAAAGTCTCGAATTTGGGTT
TGGTTCGCCGGTTACTACCCCGTCTCTCTCATCAAGTCGGCTGACCTGCCCCCTGAT
CGAAAGTACGTGTTCGGCTACCACCCTCATGGTGTTATCGGTATGGGAGCCATTGCT
AACTTTGCCACCGATGCTACTGGTTTCTCCACCCTCTTTCCCGGACTGAACCCTCAC
CTGCTCACTCTCCAGTCTAACTTCAAGCTCCCCCTGTACCGAGAGCTGCTCCTGGCC
CTGGGTATCTGCTCCGTCTCTATGAAGTCTTGTCAGAACATTCTCCGACAGGGACCT
GGTTCGGCTCTGACCATCGTCGTGGGAGGAGCTGCTGAGTCGCTCTCCGCCCATCCT
GGAACCGCTGACCTCACTCTGAAGCGACGAAAGGGCTTCATCAAGGTCGCCATTCGA
CAGGGTGCTGACCTGGTGCCCGTTTTCTCCTTTGGAGAGAACGATATTTTCGGCCAG
CTGCGAAACGAGCGAGGAACCCGACTCTACAAGCTGCAGAAGCGATTTCAGGGTGTG
TTCGGCTTCACCCTCCCTCTGTTCTACGGACGAGGCCTCTTTAACTACAACGTTGGA
CTGATGCCCTACCGACACCCTATCGTCTCGGTTGTCGGCCGACCCATTTCCGTGGAG
CAGAAGGACCATCCTACCACTGCCGATCTCGAGGAGGTGCAGGCCCGATACATCGCT
GAGCTGAAGCGAATTTGGGAGGAGTACAAGGACGCCTACGCTAAGTCTCGAACCCGA
GAGCTGAACATCATTGCCTAA Gene ID: NG68
Expression construct ID: pNC245
Donor Organism: *Lipomyces starkeyi*
Gene: DGA1
Length: 410 (amino acid); 1233 (DNA)
Function: diacylglycerol acyltransferase
Sequence Source: http://genome.jgi-psf.org/
DNA Source: Native cDNA synthesized by GenScript Protein Sequence (SEQ ID NO: 9):
MSEKAEIEVPPQKSTFPRSVHFAPLHIPLERRLQTLAVLFHTVALPYCIGLFFLMLA
FPPFWPLLVMYVIYAYGFDHSSSNGEISRRRSPLFRRLPLFRLYCDYFPIHIHREVP
LEPTPPGRLREPSGLVERWIAKMFGVQDAVVEGNESDVKATANGNGTTKEIGPTYVF
GYHPHGIVSLGAFGAIGTEGAGWEKLFPGIPVSLLTETNFSLPFYREYLLSLGIAS
VSRRSCTNLLKHDQSICIVIGGAQESLLAEPGTLDLILVKRRGFVKLAMSTARVSDQ
PICLVPILSFGENDVYDQVRGDRSSKLYKIQTFIKKAAGFTLPLMYARGIFNYDFGL
MPYRRQMTLVVGKPIAVPYVAQPTEAEIEVYHKQYMDELRRLWDTYKDDYFVDHKGK
GVKNSEMRFVE DNA Sequence (SEQ ID NO: 10):
ATGAGTGAGAAGGCAGAGATCGAGGTTCCGCCGCAAAAATCGACATTCCCTCGCAGT
GTGCACTTCGCTCCACTTCATATTCCACTGGAGAGACGCCTACAGACTTTGGCAGTC
TTATTCCACACTGTCGCGCTACCATACTGCATCGGTCTGTTCTTTCTCATGCTGGCG
TTCCCTCCTTTTTGGCCATTATTGGTAATGTATGTCATATACGCATACGGGTTCGAC
CACTCGAGCTCGAACGGAGAGATCTCCCGCCGGCGATCGCCGCTGTTTCGAAGACTC
CCGTTGTTCAGGCTGTATTGTGATTACTTCCCCATCCACATTCACCGGGAGGTTCCG
CTCGAGCCGACGTTTCCTGGTCGCCTTCGCGAACCGAGTGGCCTTGCTCGAGCGGTGG
ATTGCGAAGATGTTCGGCGTGCAGGACGCTGTTGTCGAGGGAAATGAATCTGACGTT
AAGGCCACGGCCAACGGCAATGGGACGACGAAAGAAATCGGACCGACGTATGTTTTC
GGCTATCATCCGCATGGAATTGTTAGCTTGGGTGCGTTTGGTGCTATTGGTACGGAA
GGCGCTGGATGGGAGAAGCTCTTTCCTGGGATCCCGGTGTCACTGCTGACTCTCGAA
ACAAATTTCAGCCTTCCATTTTACAGAGAGTATTTGCTGTCACTTGGGATTGCTTCA
GTATCTCGACGGTCTTGTACCAATCTCCTCAAACACGACCAATCCATCTGCATCGTT
ATCGGCGGCGCCCAAGAGTCGCTCTTAGCGGAACCAGGCACTCTAGATCTGATCCTC
GTTAAACGTCGCGGTTTTGTCAAACTTGCAATGTCAACGGCGCGGGTATCTGACCAA
CCGATTTGTCTTGTTCCGATCCTCAGTTTCGGCGAGAACGACGTGTACGACCAAGTC
CGCGGGGACCGATCGTCGAAGTTGTATAAGATCCAGACTTTTATCAAGAAAGCGGCC
GGGTTTACGCTACCATTGATGTATGCGCGCGGTATATTTAATTACGACTTTGGGCTG
ATGCCGTACCGCAGGCAAATGACGCTCGTGGTCGGCAAGCCGATTGCAGTGCCGTAC
GTGGCCCAGCCTACGGAGGCTGAAATCGAAGTGTATCACAAGCAGTACATGGATGAA
TTGAGGAGGTTATGGGACACGTATAAGGACGACTATTTTGTAGACCACAAGGGCAAG
GGGGTCAAGAATTCCGAGATGCGTTTTGTGGAGTAA TABLE 2-continued Characterization of DGA1 genes and expression constructs used herein. The map of expression constructs used to express DGA1 genes is shown on FIG. 1 with NG66 as example. The constructs for all other DGA1 genes were the same except for the DGA1 ORF.

Gene ID: NG-69
Expression construct ID: pNC270
Donor Organism: *Lipomyces starkeyi*
Gene: DGA1
Length: 410 (amino acid); 1233 (DNA)
Function: diacylglycerol acyltransferase
Sequence Source: http://genome.jgi-psf.org/
DNA Source: cDNA codon optimized for expression in *Y. lipolyica* and synthesized by GenScript Protein Sequence (SEQ ID NO: 11):
MSEKAEIEVPPQKSTFPRSVHFAPLHIPLERRLQTLAVLFHTVALPYCIGLFFLMLA
FPPFWPLLVMYVIYAYGFDHSSSNGEISRRRSPLFRRLPLFRLYCDYFPIHIHREVP
LEPTFPGRLREPSGLVERWIAKMFGVQDAVVEGNESDVKATANGNGTTKEIGPTYVF
GYHPHGIVSLGAFGAIGTEGAGWEKLFPGIPVSLLTLETNFSLPFYREYLLSLGIAS
VSRRSCTKLLKHDQSICIVIGGAQESLLAEPGTLDLILVKRRGFVKLAMSTARVSDQ
PICLVPILSFGENDVYDQVRGDRSSKLYKIQTFIKKAAGFTLPLMYARGIFNYDFGL
MPYRRQMTLVVGKPIAVPYVAQPTEAEIEVYHKQYMDELRRLWDTYKDDYFVDHKGK
GVKNSEMRFVE DNA Sequence (SEQ ID NO: 12):
ATGTCCGAGAAGGCTGAGATTGAGGTGCCCCCCCAGAAGTCTACTTTCCCTCGATCC
GTTCATTTCGCCCCCTGCATATCCCCCTGGAGCGACGACTCCAGACCCTGGCTGTG
CTCTTCCACACTGTTGCCCTGCCTTACTGCATCGGACTCTTCTTTCTGATGCTCGCT
TTCCCCCCTTTTTGGCCCCTGCTCGTGATGTACGTTATCTACGCCTACGGATTCGAC
CATTCCTCTTCGAACGGCGAGATCTCTCGACGACGATCGCCTCTGTTCCGACGACTG
CCCCTCTTTCGACTCTACTGTGATTACTTCCCTATCCACATTCATCGAGAGGTCCCC
CTGGAGCCTACCTTTCCTGGTCGACTGCGAGAGCCTTCCGGACTCGTTGAGCGATGG
ATTGCTAAGATGTTCGGTGTCCAGGACGCCGTCGTGGAGGGAAACGAGTCTGATGTG
AAGGCCACCGCTAACGGAAACGGCACCACTAAGGAGATCGGCCCTACTTACGTCTTC
GGATACCACCCCCATGGCATTGTGTCCCTGGGAGCCTTTGGCGCTATCGGTACCGAG
GGTGCTGGATGGGAGAAGCTCTTCCCTGGTATTCCCGTCTCGCTGCTCACCCTGGAG
ACTAACTTCTCCCTCCCCTTTTACCGAGAGTACCTGCTCTCTCTGGGAATCGCCTCG
GTGTCCCGACGATCGTGCACCAACCTGCTCAAGCACGACCAGTCTATCTGTATTGTT
ATCGGAGGTGCTCAGGAGTCCCTGCTCGCTGAGCCTGGAACCCTGGACCTCATTCTG
GTCAAGCGACGAGGCTTCGTGAAGCTGGCCATGTCCACTGCTCGAGTGTCTGATCAG
CCTATTTGCCTGGTTCCCATCCTCTCTTTCGGCGAGAACGACGTTTACGATCAGGTC
CGAGGTGACCGATCCTCTAAGCTGTACAAGATTCAGACCTTCATCAAGAAGGCCGCT
GGCTTTACTCTCCCTCTGATGTACGCCCGAGGCATCTTCAACTACGACTTTGGTCTG
ATGCCCTACCGACGACAGATGACCCTCGTTGTCGGCAAGCCTATTGCCGTCCCCTAC
GTGGCTCAGCCCACTGAGGCCGAGATCGAGGTCTACCACAAGCAGTACATGGACAGC
CTGCGACGACTCTGGGATACCTACAAGGACGATTACTTCGTTGACCATAAGGGCAAG
GGTGTCAAGAACTCTGAGATGCGATTTGTGGAGTAA Gene ID: NG70
Expression construct ID: pNC246
Donor Organism: *Aspergillus terreas*
Gene: DGA1
Length: 380 (amino acid); 1143 (DNA)
Function: diacylglycerol acyltransferase
Sequence Source: GenBank XP_001211961.1
DNA Source: cDNA codon optimized for expression in *Y. lipolytica* and synthesized by GenScript Protein Sequence (SEQ ID NO: 13):
MPRNTHPPANNAGPNASHKKDRKRQGRLFQHTVPNKYSRIRWAPLNIGLERRLQTLV
VLCHTLTIALFLAFFFFTCAIPLTWPLLFPYLVYITLFSTAPTSGTLKGRSDFLRSL
PIWKLYTAYFPAKLHRSEPLLPTRKYIFGYHPHGIISHGAFAAFATDALGFSKLFPG
ITNTLLTLDSNFRIPFYREYAMAMGVASVSRESCENLLTKGGADGEGMGRAITIVVG
GARESLDALPHTMRLVLKRRKGFIKLAIRTGADLVPVLAFGENDLYEQVRSDQHPLI
YKVQMLVKRFLGFTVPLFHARGIFNYDVGLMPYRRPLNIVVGRPIQVVRQQDRDKID
DEYIDRLHAEYVRELESLWDQWKDVYAKDRISELEIVA DNA Sequence (SEQ ID NO: 14):
ATGCCCCGAAACACCCACCCCCCCGCCAACAACGCCGGACCTAACGCCTCTCACAAG
AAGGACCGAAAGCGACAGGGACGACTCTTTCAGCACACCGTTCCTAACAAGTACTCT
CGAATCCGATGGGCCCCCCTCAACATTGGCCTGGAGCGACGACTGCAGACCCTCGTC
GTGCTGTGCCATACCCTCACTATCGCCCTGTTCCTCGCTTTCTTTTTCTTTACTTGT
GCCATTCCCCTGACCTGGCCTCTGCTCTTCCCCTACCTCGTGTACATCACCCTGTTT
TCGACCGCTCCTACTTCCGGTACCCTGAAGGGACGATCTGACTTCCTCCGATCGCTG
CCTATTTGGAAGCTCTACACTGCCTACTTTCCCGCTAAGCTGCACCGATCCGAGCCT
CTGCTCCCTACCCGAAAGTACATCTTCGGCTACCACCCCCATGGTATCATTTCCCAT
GGAGCCTTCGCCGCTTTTGCCACTGACGCTCTCGGCTTCTCTAAGCTGTTTCGTGGT
ATCACCAACACTCTGCTCACCCTGGATTCGAACTTCCGAATTCCCTTTTACCGAGAG TABLE 2-continued Characterization of DGA1 genes and expression constructs used herein. The map of expression constructs used to express DGA1 genes is shown on FIG. 1 with NG66 as example. The constructs for all other DGA1 genes were the same except for the DGA1 ORF.

```
TACGCCATGGCTATGGGAGTGGCTTCCGTTTCTCGAGAGTCGTGCGAGAACCTGCTC
ACTAAGGGAGGTGCTGACGGAGAGGGAATGGGCCGAGCTATCACCATTGTTGTCGGA
GGCGCCCGAGAGTCCCTCGATGCTCTGCCTCACACTATGCGACTGGTCCTCAAGCGA
CGAAAGGGTTTCATCAAGCTGGCCATTCGAACCGGAGCTGACCTCGTTCCCGTCCTG
GCCTTCGGCGAGAACGACCTCTACGAGCAGGTGCGATCTGATCAGCACCCTCTGATC
TACAAGGTCCAGATGCTCGTGAAGCGATTCCTGGGTTTTACCGTGCCCCTGTTCCAT
GCTCGAGGAATTTTTAACTACGACGTTGGCCTCATGCGTTACCGACGACCCCTGAAC
ATCGTGGTTGGTCGACCCATTCAGGTCGTGCGACAGCAGGACCGAGATAAGATCGAC
GATGAGTACATTGACCGACTCCACGCCGAGTACGTCCGAGAGCTCGAGTCCCTGTGG
GACCAGTGGAAGGATGTTTACGCCAAGGACCGAATCTCTGAGCTGGAGATTGTCGCT
TAA

Gene ID: NG71
Expression construct ID: pNC247
Donor Organism: Claviceps purpurea
Gene: DGA1
Length: 437 (amino acid); 1314 (DNA)
Function: diacylglycerol acyltransferase
Sequence Source: GenBank CCE28309.1
DNA Source: cDNA codon optimized for expression in Y. lipolytica and
synthesized by GenScript Protein Sequence (SEQ ID NO: 15):
MAAVQVARPVPPHHHDGAGREHKGERAHSPERGEKTVHNGYGLAETHEPLELNGSAV
QDGKHDSDETITNGDYSPYPELDCGKERAAHEKEAWTAGGVRFAPLRVPFKRRMQTA
AVLFHCMSIILISSCFWFSLANPITWPILVPYLVHLSLSNASTDGKLSYRSEWLRSL
PLWRLFAGYFPAKLHKTFDLPPNRKYIFGYHPHGIISHGAWCAFATNALGFVEKFPG
ITNSLLTLDSNFRVPFYRDWILAMGIRSVSRESIRNILSKGGPDSNGQGRAVTIVIG
GARESLEAQPGTLRLILQGRKGFIKVALRAGADLVPVIGFGENDLYDQLSPKTHPLV
HKIQMFFLKVFKFTIPALHGRGLLNYDVGLLPYRRAVNIVVGRPIQIDETYGEQPPA
EVIDRYHELYVQEVERLYAAYKEQFSNGKKTPELQILS DNA Sequence (SEQ ID NO: 16):
ATGGCTGCTGTTCAGGTTGCCCGACCCGTTCCCCCCCACCACCACGATGGCGCTGGC
CGAGAGCACAAGGGAGAGCGAGCCCATTCCCCTGAGCGAGGAGAGAAGACCGTCCAC
AACGGCTACGGTCTGGCCGAGACTCATGAGCCCCTGGAGCTCAACGGTTCTGCTGTG
CAGGACGGAAAGCACGACTCGGATGAGACCATCACTAACGGTGACTACTCTCCCTAC
CCTGAGCTCGATTGCGGAAAGGAGCGAGCCGCTCATGAGAAGGAGGCTTGGACCGCT
GGAGGTGTGCGATTCGCTCCTCTGCGAGTTCCTTTTAAGCGACGAATGCAGACTGCC
GCTGTCCTCTTCCACTGCATGTCCATCATTCTGATTTCCTCTTGTTTCTGGTTTTCT
CTCGCCAACCCCATCACCTGGCCTATTCTCGTTCCCTACCTGGTCCACCTGTCGCTC
TCCAACGCTTCTACTGACGGCAAGCTCTCCTACCGATCTGAGTGGCTGCGATCCCTG
CCTCTCTGGCGACTGTTCGCCGGTTACTTTCCCGCTAAGCTCCACAAGACCTTCGAT
CTGCCCCCTAACCGAAAGTACATCTTTGGTTACCACCCCCATGGAATCATTTCCCAT
GGCGCTTGGTGTGCCTTCGCTACCAACGCTCTGGGCTTCGTTGAGAAGTTTCCTGGT
ATTACCAACTCGCTGCTCACTCTCGACTCCAACTTCCGAGTGCCCTTTTACCGAGAT
TGGATCCTGGCCATGGGCATTCGATCTGTTTCGCGAGAGTCTATCCGAAACATTCTC
TCGAAGGGAGGACCTGACTCCAACGGACAGGGCCGAGCTGTGACCATCGTTATTGGT
GGAGCCCGAGAGTCTCTGGAGGCTCAGCCCGGAACTCTGCGACTCATTCTGCAGGGC
CGAAAGGGCTTCATTAAGGTGGCTCTCCGAGCTGGAGCTGACCTGGTTCCCGTCATC
GGTTTCGGAGAGAACGACCTCTACGATCAGCTGTCCCCTAAGACCCACCCCCTCGTT
CATAAGATCCAGATGTTCTTTCTGAAGGTCTTCAAGTTTACTATTCCTGCTCTGCAC
GGACGAGGTCTGCTCAACTACGACGTCGGTCTGCTCCCTTACCGACGAGCTGTGAAC
ATCGTCGTGGGACGACCCATCCAGATTGACGAGACCTACGGCGAGCAGCCCCCTCAG
GAGGTCATCGATCGATACCACGAGCTCTACGTCCAGGAGGTGGAGCGACTGTACGCC
GCTTACAAGGAGCAGTTCTCGAACGGAAAGAAGACCCCCGAGCTCCAGATCCTGTCC
TAA Gene ID: NG72
Expression construct ID: pNC248
Donor Organism: Aurantiochytriun limacinum
Gene: DGA1
Length: 351 (amino acid); 1056 (DNA)
Function: diacylglycerol acyltransferase
Sequence Source: http://genome.jgi-psf.org/
DNA Source: cDNA codon optimized for expression in Y. lipolytica and
synthesized by GenScript Protein Sequence (SEQ ID NO: 17):
MLAWMPVLIALPRRKQTAVVLLFVMLLPMIMVVYSWTLILLIFPLTTLPTLSYLIWI
MYIDKSHETGKRKPFMRYWKMWRHFANYFPLRLIRTTPLDPRRKYVPCYHPHGIISL
GAFGNFATDSTGFSRKFPGIDLRLLTLQINFYCPIIRELLLYMGLCSAAKKSCNQIL
QRGPGSAIMLVVGGAAESLDSQPGTYRLTLGRKGEVRVALDNGADLVPVLGFGENDV
FDTVYLPPNSWARNVQEFVRKKLGFATPIFSGRGIFQYNMGLMPHRKPIIVVVGKPI
```

TABLE 2-continued

Characterization of DGA1 genes and expression constructs used herein. The map of expression constructs used to express DGA1 genes is shown on FIG. 1 with NG66 as example. The constructs for all other DGA1 genes were the same except for the DGA1 ORF.

KIPKIPDELKGRALSTTAEGVALVDKYHEKYVRALRELWNLYKEEYATEPKAAYLEP
NSIRKNQNV

DNA Sequence (SEQ ID NO: 18):
```
ATGCTCGCCTGGATGCCTGTCCTCATTGCCCTCCCCCGACGAAAGCAGACCGCTGTT
GTTCTCCTGTTTGTGATGCTCCTCCCTATGATCATGGTCGTGTACTCCTGGACCCTG
ATCCTGCTCATTTTCCCCCTCACCACTCTGCCTACTCTCTCCTACCTGATCTGGATT
ATGTACATTGACAAGTCTCACGAGACCGGAAAGCGAAAGCCCTTTATGCGATACTGG
AAGATGTGGCGACATTTCGCCAACTACTTTCCTCTCCGACTGATCCGAACCACTCCC
CTGGACCCTCGACGAAAGTACGTGTTCTGCTACCACCCCCATGGCATCATTTCCCTC
GGAGCCTTCGGCAACTTTGCTACCGACTCGACTGGCTTCTCCCGAAAGTTTCCCGGT
ATCGATCTGCGACTGCTCACCCTCCAGATTAACTTCTACTGTCCTATCATTCGAGAG
CTGCTCCTGTACATGGGTCTGTGCTCTGCCGCTAAGAAGTCGTGTAACCAGATCCTC
CAGCGAGGACCCGGCTCTGCTATTATGCTGGTTGTCGGCGGTGCCGCTGAGTCCCTC
GACTCTCAGCCTGGCACCTACCGACTCACTCTGGGTCGAAAGGGATTCGTGCAGTT
GCCCTGGACAACGGTGCTGATCTGGTCCCCGTGCTCGGTTTCGGAGAGAACGACGTG
TTTGATACCGTTTACCTGCCCCCTAACTCGTGGGCCCGAAACGTCCAGGAGTTCGTG
CGAAAGAAGCTCGGATTCGCTACCCCCATCTTTTCCGGCCGAGGTATTTTTCAGTAC
AACATGGGTCTGATGCCCCACCGAAAGCCTATCATTGTGGTTGTCGGAAAGCCCATC
AAGATTCCCAAGATCCCTGACGAGCTGAAGGGACGAGCCCTCTCTACCAC7GCCGAG
GGCGTTGCTCTGGTCGATAAGTACCATGAGAAGTACGTTCGAGCCCTCCGAGAGCTG
TGGAACCTCTACAAGGAGGAGTACGCTACCGAGCCCAAGGCCGCTTACCTCGAGCCT
AACTCGATTCGAAAGAACCAGAACGTCTAA
```

Example 2: Recombinant Yeast Host Cell Having Increased Lipid Production

A total of nine different DGA1 genes were expressed in *Y. lipolytica* under the same strong *Y. lipolytica* GPD1 promoter (Table 2 and FIG. 1). FIG. 1 shows expression construct pNC243 used for overexpression of *R. toruloides* DGA1 gene NG66 in *Y. lipolytica*. All other DGA1 expression constructs were the same as pNC243 except for the DGA1 ORFs that are described in the Table 2. DGA1 expression constructs were linearized before transformation by PacI/NotI restriction digest (FIG. 1). The linear expression constructs each included expression cassette for DGA1 gene and for NatI gene, used as marker for selection with nourseothricin (NAT). Expression contracts were randomly integrated into genome of *Y. lipolytica* strain NS18 (obtained from ARS Culture Collection, NRRL #YB 392) using transformation protocol as described in Chen (Chen D C, et al. One-step transformation of the dimorphic yeast *Yarrowia lipolytica*. Appl Microbiol Biotechnol. 1997 August; 48(2): 232-5). Transformants were selected on YPD plates with 500 µg/mL NAT and screened for ability to accumulate lipids by fluorescent staining lipid assay described below. For each expression construct eight transformants were analyzed. The results of the lipid assay are shown on the FIG. 2. In this experiment the presence of heterologous DGA1 in *Y. lipolytica* was not confirmed by colony PCR. For most constructs, there was significant colony variation between transformants probably due to lack of functional DGA1 expression cassette in some transformants that only obtained functional Nat1 cassette, or due to negative effect of DGA1 site of integration on DGA1 expression. Nevertheless, data in FIG. 2 demonstrate that all nine DGA1 genes had significant positive effect on lipid content in *Y. lipolytica*. Overexpression of native *Y. lipolytica* DGA1 under a strong promoter increased lipid content measured by cell fluorescence by about 2-fold compared to the parental strain NS18. Transformants that demonstrated the highest fluorescence (about 3-fold higher compared to NS18) were generated by overexpression of *R. toruloides* DGA1 (NG66, NG67) and *L. starkeyi* DGA1 (NG68). The most effective DGA1 genes came from the donors that were repeatedly reported to be the most oleaginous yeast among other oleaginous yeast strains. This result may indicate that in oleaginous yeast DGA1 gene product activity and/or expression level may be the factor that determines lipid production level. In certain experiments, the effect of native *R. toruloides* DGA1 (NG49) overexpression on lipid production in *Y. lipolytica* was not as high as the effect of synthetic versions of *R. toruloides* DGA1 genes that did not contain introns. This result may indicate that the gene splicing of the heterologous *R. toruloides* DGA1 gene in *Y. lipolytica* was not very efficient. In certain experiments, codon optimization of *R. toruloides* and *L. starkeyi* DGA1 genes for expression in *Y. lipolytica* did not have positive effect on lipid production. For *L. starkeyi* DGA1, codon optimized version of the gene (NG69) was less effective than *L. starkeyi* cDNA sequence NG68 with native codons.

Figure 2:
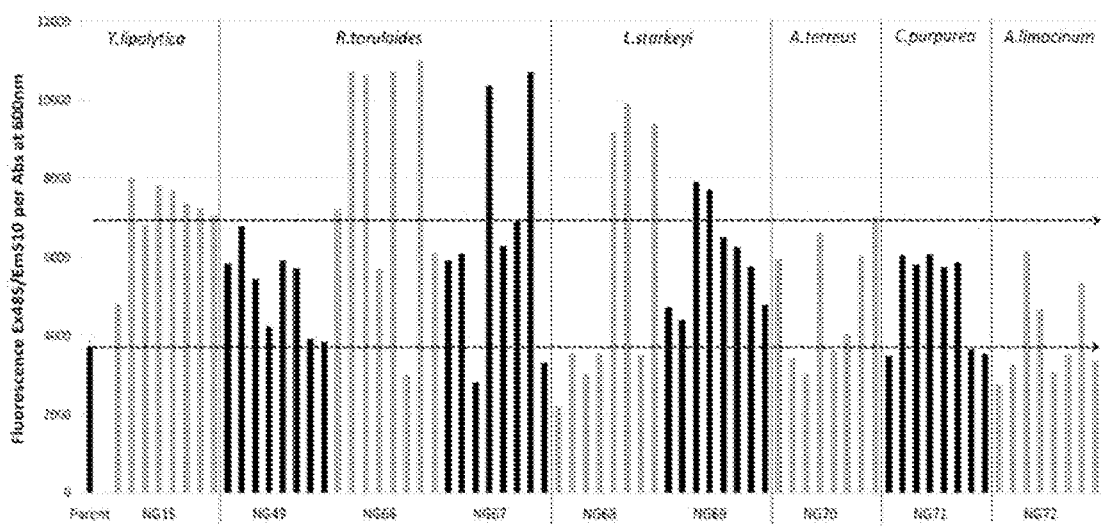
FIG. 2 shows the results for a 96-well plate lipid assay for NS18 transformants with randomly integrated DGA1 genes. The DGA1 genes are described in Table 2. The *Y. lipolytica* NS18 strain was used as the parent strain. The expression construct used to integrate randomly DGA1 genes into NS18 genome is shown on FIG. 1.
Figure 3:
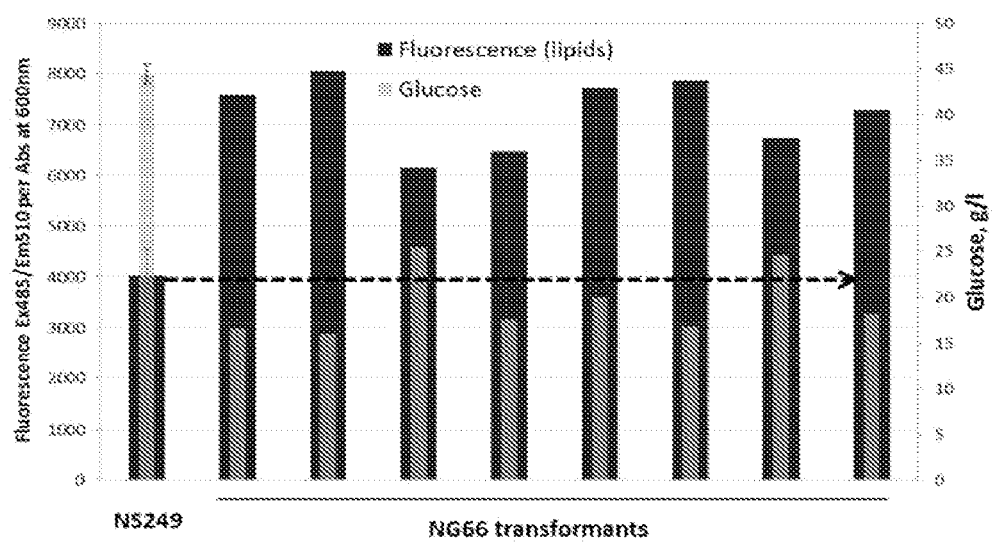
FIG. 3 shows the results for a shake flask lipid assay for NS18 transformants with randomly integrated NG15 gene (NS249 strain) and NG66 gene. NS249 was selected by lipid assay as the best NS18+NS15 transformant out of 50 transformants screened (data not shown). Eight NS18+NG66 transformants were selected by lipid assay out of 80 transformants screened (data not shown). The expression construct used to integrate randomly DGA1 genes into NS18 genome is shown in FIG. 1.

In order to confirm data shown on FIG. 2 and select transformants with the highest lipid production level, more transformants were screened for *Y. lipolytica* DGA1 gene NG15 and *R. toruloides* DGA1 gene NG66. For NG15, about 50 colonies were screened by lipid assay for highest lipid accumulation and the best transformant was named NS249 (data not shown). For NG66, 80 colonies were screened and 8 best colonies were selected for further analysis (data not shown). Strain NS249 and 8 selected transformants expressing NG66 were grown in shake flasks and analyzed by lipid assay for lipid content and HPLC for glucose consumption (Example 6). The results of the experiment are shown on FIG. 3. FIG. 3 demonstrated that *Y. lipolytica* strains overexpressing *R. toruloides* DGA1 have significantly higher lipid content compared to NS249 with native *Y. lipolytica* DGA1 gene expressed under the same promoter as *R. toruloides* DGA1. At the same time, NG66 transformants have significantly less glucose left in the media compared to NS249, demonstrating that NG66 was more efficient in converting glucose to lipids than *Y. lipolytica* DGA1 gene NG15. The difference in efficiency between two DGA1 genes may be attributed to either higher level of expression of R. toruloides DGA1 in Y. lipolytica or higher level of R. toruloides DGA1 specific activity, or both.

Example 4: Lipid Assay

1. Prepare growth medium:

| | |
|---|---|
| Urea | 0.5 g/L |
| Yeast extract | 1.5 g/L |
| Casamino Acids | 0.85 g/L |
| Yeast Nitrogen Base (YNB w/o a.a. and ammonium sulfate | 1.7 g/L |
| Glucose | 100 g/L |
| Potassium Hydrogen Phthalate buffer pH 5.5 | 5.11 g/L (25 mM) |
| Filter sterilize | |

2. Plate strains to analyze on YPD or other appropriate media and incubate 1-2 days at 30° C.
3. Fill autoclaved 250 mL flasks, 24-, 48- or 96-well plates with medium:
    flasks: 50 mL per flask
    96-well plate: 300 µL per well
4. Cover the flask with aluminum foil and the plates with porous covers.
5. Incubate with shaking at 30° C. for 72 to 96 hours
    flasks: 200 rpm in New Brunswick Scientific shaker
    plates: 900 rpm, 70-90% humidity in Infors Multitron ATR shaker
6. Mix 20 µL cells with 20 µL of 100% ethanol in analytical microplate and incubate at 4° C. for 30 minutes
7. Set up master mix (80 µL per reaction):

| | |
|---|---|
| 1M Potassium Iodide | 50 µL |
| 1 mM Bodipy 493/503*** | 1 µL |
| 100% DMSO | 0.5 µL |
| 60% PEG 4000 | 1.5 µL |
| Water | 27 µL |

8. Aliquot master mix into Costar Black well/clear bottom plate (800 µL/well)
9. Add 20 µL of ethanol/cells mix and cover with transparent seal
10. Measure fluorescence with SpectraMax M2 spectrophotometer (Molecular Devices) with following setup:
    kinetic assay
    read FL 485/510 with 495 cutoff
    mix 5 seconds before each read
    Select Costar Black well/clear bottom plate
    Deselect autocalibrate
    30 min experiment, reading every minute
    Heat chamber to 30° C.
11. Measure OD in the same plate with following setup:
    Absorbance 600 nm
    mix 5 seconds before each read
    Select Costar Black well/clear bottom plate
    Deselect autocalibrate
    Heat chamber to 30° C.
Calculate normalized fluorescence by dividing fluorescence at 30 min by OD.

INCORPORATION BY REFERENCE

All of the U.S. patents, U.S. published patent applications, and published PCT applications that cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

What is claimed is:

1. A recombinant *Yarrowia* yeast cell comprising a heterologous polynucleotide comprising a nucleic acid molecule encoding a heterologous polypeptide having diacylglycerol acyltransferase activity and comprising an amino acid sequence having at least 90% sequence identity to the amino acid sequence set forth in SEQ ID NO: 5, SEQ ID NO: 9, SEQ ID NO: 13, SEQ ID NO: 15, or SEQ ID NO: 17, or a biologically-active portion thereof, wherein the recombinant yeast cell has a higher lipid content than a non-recombinant yeast cell of the same species, and wherein the biologically active portion is 278 contiguous amino acids of SEQ ID NO: 5, SEQ ID NO: 9, SEQ ID NO: 13, SEQ ID NO: 15, or SEQ ID NO: 17.

2. The recombinant *Yarrowia* yeast cell of claim 1, wherein the nucleic acid molecule comprises at least 95% sequence identity to the nucleotide sequence of SEQ ID NO: 6, SEQ ID NO: 8, SEQ ID NO: 10, SEQ ID NO: 12, SEQ ID NO: 14, SEQ ID NO: 16, or SEQ ID NO: 18.

3. The recombinant *Yarrowia* yeast cell of claim 1, wherein the nucleic acid molecule comprises a nucleotide sequence of SEQ ID NO: 6, SEQ ID NO: 8, or SEQ ID NO: 10.

4. The recombinant *Yarrowia* yeast cell of claim 1, wherein said *Yarrowia* yeast is oleaginous, high-temperature tolerant, or both.

5. The recombinant *Yarrowia* yeast cell of claim 1, wherein the *Yarrowia* yeast cell is *Yarrowia lipolytica*.

6. A method for producing lipids using a recombinant *Yarrowia* yeast cell comprising:
   a) providing a recombinant *Yarrowia* yeast cell comprising:
   a heterologous polynucleotide comprising a nucleic acid molecule encoding a heterologous DGA1 polypeptide having diacylglycerol acyltransferase activity and comprising an amino acid sequence having at least 90% sequence identity to the amino acid sequence set forth in SEQ ID NO: 5, SEQ ID NO: 9, SEQ ID NO: 13, SEQ ID NO: 15, or SEQ ID NO: 17, or a biologically-active portion thereof, and wherein the biologically active portion is 278 contiguous amino acids of SEQ ID NO: 5, SEQ ID NO: 9, SEQ ID NO: 13, SEQ ID NO: 15, or SEQ ID NO: 17; and
   b) growing the cell of step (a) under conditions whereby the nucleic acid molecule encoding DGA1 polypeptide is expressed, thereby producing lipids.

7. The method of claim 6, wherein the recombinant *Yarrowia* yeast cell is *Y. lipolytica*.

8. The method of claim 6, wherein the nucleic acid molecule comprises at least 95% sequence identity to the nucleotide sequence of SEQ ID NO: 6, SEQ ID NO: 8, SEQ ID NO: 10, SEQ ID NO: 12, SEQ ID NO: 14, SEQ ID NO: 16, or SEQ ID NO: 18.

9. The method of claim 6, wherein the polynucleotide is selected from the group consisting of the nucleotide sequence set forth in SEQ ID NO: 6, SEQ ID NO: 8, and SEQ ID NO: 10.

10. The method of claim 6, wherein the recombinant *Yarrowia* yeast cell is grown in the presence of a substrate selected from the group consisting of glucose, ethanol, xylose, sucrose, starch, starch dextrin, glycerol, cellulose, and acetic acid.

11. The recombinant *Yarrowia* yeast cell of claim 1, wherein the heterologous polypeptide comprises the amino acid sequence set forth in SEQ ID NO: 9.

12. The recombinant *Yarrowia* yeast cell of claim 1, wherein the nucleic acid molecule comprises the nucleotide sequence of SEQ ID NO: 10.

13. The recombinant *Yarrowia* yeast cell of claim 1, wherein the heterologous polypeptide comprises an amino acid sequence set forth in SEQ ID NO: 5, SEQ ID NO: 9, SEQ ID NO: 13, SEQ ID NO: 15, or SEQ ID NO: 17.

14. The method of claim 6 further comprising recovering the lipids of step (b).

15. The method of claim 6, wherein the DGA1 polypeptide comprises the amino acid sequence set forth in SEQ ID NO: 5, SEQ ID NO: 9, SEQ ID NO: 13, SEQ ID NO: 15, or SEQ ID NO: 17.

* * * * *